(12) United States Patent
Gazic Smilovic et al.

(10) Patent No.: US 8,785,674 B2
(45) Date of Patent: *Jul. 22, 2014

(54) PROCESS FOR HYDROGENATION OF HALOGENOALKENES WITHOUT DEHALOGENATION

(75) Inventors: Ivana Gazic Smilovic, Ljubljana (SI); Zdenko Casar, Ljubljana (SI)

(73) Assignee: Lek Pharmaceuticals D.D., Ljubljana (SL)

( * ) Notice: Subject to any disclaimer, the term of this patent is extended or adjusted under 35 U.S.C. 154(b) by 162 days.

This patent is subject to a terminal disclaimer.

(21) Appl. No.: 13/379,171

(22) PCT Filed: Jun. 18, 2010

(86) PCT No.: PCT/EP2010/058672
§ 371 (c)(1),
(2), (4) Date: May 11, 2012

(87) PCT Pub. No.: WO2010/146176
PCT Pub. Date: Dec. 23, 2010

(65) Prior Publication Data
US 2012/0220794 A1 Aug. 30, 2012

(30) Foreign Application Priority Data

Jun. 19, 2009 (EP) .................................. 09163227
Jul. 27, 2009 (EP) .................................. 09166475
Dec. 21, 2009 (EP) .................................. 09180099

(51) Int. Cl.
*C07F 5/02* (2006.01)

(52) U.S. Cl.
USPC ........................................................ 558/288

(58) Field of Classification Search
None
See application file for complete search history.

(56) References Cited

U.S. PATENT DOCUMENTS

| | | | | |
|---|---|---|---|---|
| 5,637,782 A * | 6/1997 | Kalnes | ........................... | 570/262 |
| 2001/0012907 A1 | 8/2001 | Sato | | |
| 2003/0008828 A1 | 1/2003 | Priestley | | |

FOREIGN PATENT DOCUMENTS

| | | |
|---|---|---|
| EP | 0126501 A2 | 11/1984 |
| WO | WO 2005/097809 A2 | 10/2005 |
| WO | WO 2009/004350 A1 | 1/2009 |

OTHER PUBLICATIONS

Wang Z et al, "A New and Practical Synthesis of Vinyl Dichlorides via a non-Wittig-type approach",Tetrahedron Letters, vol. 41, No. 21, May 1, 2000, pp. 4007-4009.
Matteson D S et al, "(R)-1-Acetamido-2-phenylethaneboronic acid". A specific transition-state analog for chymotrypsin, Journal of the American Chemical Society, vol. 103, No. 17, Aug. 26, 1981, pp. 5241-5242.
Reppe W et al; "Vinylierung", Justus Liebigs Annalen Der Chemie, vol. 601, 1956, pp. 81-138.
Baganz H et al, "Über 1-Phenoxy-2-äthoxy-äthen =1-Phenoxy-2-ethoxyethene", Chemische Berichte. vol. 86, No. 10, Oct. 1953, pp. 1318-1322.
Shostakovskii M F et al, "Synthesis and Transformations of Organosilicon Vinyl Ethers", Journal of General Chemistry of the USSR, vol. 29, 1959, pp. 370-379.
Kalabina A V et al, "Synthesis and Derivatives of Vinyl Ethers of Chlorophenols", Izvestiya Sibirskogo Otdeleniya Akademii Nauk SSSR, 1958, pp. 9-16.
Reppe W et al, "Äthinylierung V. Reaktionen Hydrierter Äthinylierungsprodukte Dehydratisierung von y-Alkandiolen = Ethynylation. V. Reactions of Hydrated Ethynylation Products. Dehydration of y-alkanediols", Justus Liebigs Annalen Der Chemie, vol. 596, 1955, pp. 80-158.
Deloux L et al, "Stereospecific Synthesis of Temarotene, Its Structural Isomers, and Mixed Triaryl Alkenes from gem-Borazirconocene Alkenes" Journal of Organic Chemistry, vol. 60, No. 11, Jun. 2, 1995, pp. 3276-3277.
Desurmont G et al, "Zirconocene-Mediated Preparation of 1 , 3-, 1, 4-, and 2, 3- Dibora-1, 3-butadienes: Their Isolation and Characterization and Use in Suzuki-Miyaura Coupling" Organometallics, vol. 15, No. 15, Jul. 23, 1996, pp. 3323-3328.
Eddarir S et al, "Regiospecific Synthesis of Symmetrical (1 E,3E) 2,3-difluoro-1,4-diphenyl-buta-1 ,3-dienes via palladium-catalyzed cross-coupling of (Z) 2-bromo-2-fluoroethenylbenzenes in presence of bis(pinacolato)diboron" Journal of Fluorine Chemistry, vol. 125, No. 3, Mar. 1, 2004, pp. 377-380.
Bhat N G et al, "A Novel Synthesis of (E)-gem-Dimetalloalkenes Containing Boron and Silicon: An Easy Access to Alkyl Trimethylsilyl Ketones" SYNLETT, No. 2, 2004, pp. 297-298.
Bhat N G et al, "A Novel Synthesis of β-ketosilanes via Organoboranes" Tetrahedron Letters, vol. 41, No. 34, Aug. 19, 2000, pp. 6541-6544.

(Continued)

*Primary Examiner* — Brandon Fetterolf
*Assistant Examiner* — Ana Z Muresan
(74) *Attorney, Agent, or Firm* — Arent Fox LLP

(57) ABSTRACT

A process for preparing a compound of formula VI

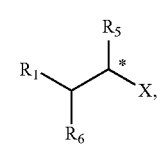

VI wherein
$R_1$ and $R_6$ is hydrogen, substituted or unsubstituted alkyl substituted or unsubstituted aryl, or substituted or unsubstituted aralkyl;
$R_5$ is $B(OR_2)(OR_3)$, or
wherein $R_2$ and $R_3$ independently from each other represent substituted or unsubstituted alkyl, substituted or unsubstituted aryl, or substituted or unsubstituted aralkyl; or $R_2$ and $R_3$ cooperatively form a part of a 5- to 10-membered fused or unfused ring, optionally a chiral 5- to 10-membered fused or unfused ring;
X is selected from Cl, Br, I; and
* indicates a chiral center;
is described.

17 Claims, No Drawings

(56) References Cited

OTHER PUBLICATIONS

Batey R A et al, "Alkenyl and Aryl Boronates—Mild Nucleophiles for the Stereoselective Formation of Functionalized N-heterocycles" Journal of the American Chemical Society, vol. 121, No. 21, Jun. 2, 1999, pp. 5075-5076.

Lhermitte F et al, "Radical Reactions in Organoboron Chemistry. III -Addition Reactions to Alkynylboranes as Efficient Routes to New Regio- and Stereodefined Alkenyl Diamino- and Dialkoxyboranes" SYNLETT, No. 4, Apr. 1996, pp. 377-379.

Trost B M et al, "Nickel Catalysed Coupling of Allylamines and Boronic Acids" Journal of the Chemical Society, Perkin Transactions 1, No. 17, 1995, pp. 2083-2096.

Brown H C et al, "A Convenient Synthesis of Alpha,Gamma-Unsaturated Ketones via Allylation of Z-1-Halo-1-Alkenyl-1 ,3,2-Dioxaborolane" Tetrahedron Letters, vol. 35, No. 38, Sep. 19, 1994, pp. 6963-6966.

Kamabuch I A et al, "Synthesis of Functionalized 1-alkenylboronates via hydroboration-dealkylation of alkynes with diisopinocampheylborane" Synthetic Communications, vol. 23, No. 20, 1993, pp. 2851-2859.

Waas J R et al, "Preparation and reaction of 1, 1-zinc, boron and 1, 1-copper, boron alkenyl bimetallics" Tetrahedron Letters, vol. 33, No. 26, Jun. 23, 1992, pp. 3717-3720.

Brown H C et al, "Vinylic Organoboranes. 7. Stereoselective Synthesis of (E)-(1Substituted-1-alkenyl)boronic esters by the Nucleophilic Substitution of (2)-1-(Bromo-1-alkenyl)boronic esters with Organolithium or Grignard Reagents. Isolation and Oxidation to Ketones" Journal of Organic Chemistry, vol. 51, No. 26, Dec. 1986, pp. 5277-5282.

Brown H C et al, "Organoboranes. 37. Synthesis and Properties of (Z)-1-Alkenylboronic Esters" Organometallics, vol. 3, No. 9, Sep. 1984, pp. 1392-1395, DOI: 10.1021/om00087a013.

Brown H C et al, "Organoboranes. 30. Convenient Procedures for the Synthesis of Alkyl -and Alkenylboronic Acids and Esters" Organometallics, vol. 2, No. 10, Oct. 1983, pp. 1311-1316.

Schaumberg G D et al, "Dibutyl cis- and trans-1-butene-1-boronate" Journal of Organometallic Chemistry, vol. 20, No. 1, Nov. 1, 1969, pp. 261-263.

Matteson D S et al, "Dibutyl Acetyleneboronate: Preparation and Some Additions of Free Radicals" Journal of Organic Chemistry, vol. 28, Feb. 1963, pp. 369-371.

Matteson D S et al, "R-1-Acetamido-2-phenylethaneboronic acid. A specific transition-state analog for chymotrypsin" Journal of the American Chemical Society, vol. 103, No. 17, Aug. 1981, pp. 5241-5242.

Kettner C A et al, "Inhibition of the serine proteases leukocyte elastase, pancreatic elastase, cathepsin G, and chymotrypsin by peptide boronic acids" Journal of Biological Chemistry, vol. 259, No. 24, Dec. 25, 1984, pp. 15106-15114.

Satoh M et al, "Stereo- and regiospecific synthesis of trisubstituted alkenes via the palladium-catalyzed cross-coupling reaction of diisopropyl (E)-(1-alkyl-1-alkenyl) boronates with organic halides" Chemistry Letters, vol. 15, No. 8, Aug. 5, 1986, pp. 1329-1332.

Kim B J et al, "Conversion of alkyltrifluoroborates into alkyltrifluorosilane with tetrachlorosilane in coordinating solvents", Angewandte Chemie, International Edition, vol. 43, No. 23, Jun. 7, 2004, pp. 3056-3058.

Matteson D S, et al, "Cesium alkyltrifluoroborates from asymmetric boronic esters", SYNLETT, No. 20, Dec. 18, 2006, pp. 3501-3503.

* cited by examiner

_US 8,785,674 B2_

PROCESS FOR HYDROGENATION OF HALOGENOALKENES WITHOUT DEHALOGENATION

CROSS-REFERENCE TO RELATED APPLICATION

This application is a National Stage entry of International Application No. PCT/EP2010/058672, filed Jun. 18, 2010, which claims priority to European Application Nos. 09163227.3, filed Jun. 19, 2009, 09166475.5, filed Jul. 27, 2009, 09180099.5, filed Dec. 21, 2009, the entire specifications, claims and drawings of which are incorporated herewith by reference.

FIELD OF THE INVENTION

The present invention relates in general to the field of organic chemistry and in particular to the preparation of chiral halogenoalkanes. These compounds are useful, for example, as intermediates in the synthesis of pharmaceutical active compounds. For example, α-halogeno boronic esters can be used for preparing boronic acid and ester compounds such as N-terminal peptidyl boronic acid derivatives, for example N-(pyrazin-2-yl)carbonyl-L-phenylalanine-L-leucine boronic acid, i.e. bortezomib.

BACKGROUND OF THE INVENTION

Hydrogenation step(s), in particular in the preparation of pharmaceutical active compounds and intermediates thereof, is(are) (a) common mean(s) for preparing halogenoalkanes. However, there are still problems involved with homogeneous catalyzed hydrogenation step(s), especially depending on the type of substituents at the C,C-double bond moiety and in particular when halogen like chlorine, bromine or iodine is attached directly to C,C-double bond moiety. Therefore, there is a need to improve such hydrogenation step(s).

Thus, a particular object of the present invention is a process that would enable hydrogenation of halogenoalkenes without dehalogenation

SUMMARY OF THE INVENTION

The present invention provides the following items including main aspects and preferred embodiments, which respectively alone and in combination particularly contribute to solving the above object and eventually provide additional advantages:

(1) A process for preparing a compound of formula VI

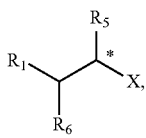

wherein
$R_1$ and $R_6$ is hydrogen, substituted or unsubstituted alkyl substituted or unsubstituted aryl, or substituted or unsubstituted aralkyl;
$R_5$ is $OR_2$, $NR_2R_3$, $SR_2$, $B(OR_2)(OR_3)$, or X" selected from F, Cl, Br, I, $OCOR_2$, $OSO_2R_2$,
wherein $R_2$ and $R_3$ independently from each other represent substituted or unsubstituted alkyl, substituted or unsubstituted aryl, or substituted or unsubstituted aralkyl; or $R_2$ and $R_3$ cooperatively form a part of a 5- to 10-membered fused or unfused ring, optionally a chiral 5- to 10-membered fused or unfused ring;
X is selected from F, Cl, Br, I; and
* indicates a chiral center;
by hydrogenation of a compound of formula V

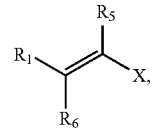

wherein $R_1$, $R_5$, $R_6$ and X are as defined above;
wherein hydrogenation is conducted in the presence of a catalyst selected from complexes comprising at least one transition metal.

The term "alkyl" as employed herein includes both straight and branched hydrocarbon chains of up to 12 carbons, preferably 1-8 carbons, such as methyl, ethyl, propyl, i-propyl, butyl, t-butyl, i-butyl, pentyl, hexyl, i-hexyl, heptyl, 4,4-dimethylpentyl, octyl, 2,2,4-trimethylpentyl, nonyl, decyl, undecyl and dodecyl, or cyclic hydrocarbons including saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" as employed herein by itself or as part of another group refers to monocyclic or bicyclic aromatic groups containing from 6 to 12 carbons in the ring portion, preferably 6-10 carbons in the ring portion, such as phenyl or naphthyl.

The term "arylalkyl" as used herein means that the aforementioned aryl moieties are incorporated into the aforementioned straight or branched alkyl moieties either at one of the proximal or distal ends of the alkyl chain or between the aforementioned alkyl chains. For example, proximal end means for $R_1$ e.g. adjacent to the double bond of compound of formula V, and for $R_2$ and $R_3$ adjacent to the oxygen of compound of formula V and VI, while distal means the terminal end of the arylalkyl moiety.

The term "substituted" as employed herein includes alkyl, aryl or aralkyl groups as defined above that have one, two or three halogen substituents, or one $C_{1-6}$ alkyl($C_{6-10}$)aryl, halo($C_{6-10}$)aryl, $C_{3-8}$ cycloalkyl, $C_{1-6}$ alkyl($C_{3-8}$)cycloalkyl, $C_{2-8}$ alkenyl, $C_{2-8}$ alkynyl, hydroxy and/or carboxy.

The term "fused" as used herein means at least two rings connected one to the other with at least one common bond.

Compound of formula V may be in form of a mixture of both (E) and (Z) isomers or in form of pure (E) and (Z) isomer respectively.

The procedural concept according to this aspect of the invention involving conversion of compound of formula V to compound of formula VI provides for an industrially applicable and competitive process, since the use of toxic and/or hazardous reagents can be avoided, wherein choosing compound of formula V as the starting material enables the use of inexpensive and readily available prior starting materials to obtain highly desirable intermediate compounds for further synthesis, e.g. synthesis of pharmaceutical active comounds. Furthermore, other methods that could provide compounds VI, like halogenation of chiral alcohols usually, do not retain chirality on the chiral center rendering these approaches unpractical.

$R_2$ and $R_3$ may be selected in view of subsequent procedural steps. For example, in case $R_2$ and $R_3$ are used as protecting group(s) only, e.g. for protection of a boronic acid moiety, achiral $R_2$ and $R_3$ may be used which can be introduced by readily available and/or inexpensive reagents. On the other hand, if $R_2$ and $R_3$ represent an integral part of the compound to be produced, or if $R_2$ and $R_3$ act as directing group(s), then suitable chiral group(s) may be selected for $R_2$ and $R_3$.

(2) The process according to item (1), wherein dehalogenation occurs in less than 10 molar % relative to the molar amount of the compound of formula VI The term "dehalogenation" as used herein means a reaction wherein a halogen is removed from a compound and replaced by hydrogen.

According to this preferred embodiment of the invention, it has been surprisingly found that substituted compounds of formula V can be hydrogenated to arrive at hydrogenated compounds of formula VI without a substantial risk of dehalogenation. By further choosing a suitable catalyst which provides for mild reaction conditions, dehalogenation of compounds of formula V can be essentially avoided.

(3) The process according to item (1) or (2), wherein $R_5$ is $B(OR_2)(OR_3)$.

According to this beneficial embodiment of the invention, conversion of compound of formula V to compound of formula VI provides for an industrially applicable and competitive process for the preparation of α-substituted boronic esters, since—in contrast to the Matteson's methodology, which is used in prior art (see e.g. WO2005/097809 A2, in *J. Biol. Chem.* 1984, 259, 15106-15114 and in *J. Am. Chem. Soc.* 1981, 103, 5241-5242) to obtain such compounds—there is no difficulty to control rearrangement step. Furthermore, choosing compound of formula V as the starting material enables the use of inexpensive and readily available prior starting materials to obtain such a compound, while the use of toxic and/or hazardous reagents can be avoided.

(4) The process according to any one of the preceding items, wherein X is selected from Cl, Br, I.

(5) The process according to any one of the preceding items, wherein $R_1$ or/and $R_6$ is/are (independently from each other) selected from hydrogen or a group consisting of substituted or unsubstituted linear $C_1$-$C_5$-alkyl, substituted or unsubstituted branched $C_1$-$C_5$-alkyl and substituted or unsubstituted $C_3$-$C_8$-cycloalkyl, preferably $R_1$ or/and $R_6$ is/are (independently from each other) selected from hydrogen or unsubstituted linear or branched $C_1$-$C_5$-alkyl, more preferably $R_1$ and/or $R_6$ is/are hydrogen or isopropyl; and/or wherein either $R_1$ or $R_6$ is hydrogen, preferably $R_6$ is hydrogen; and/or wherein $R_2$ and $R_3$ are selected from a group consisting of linear substituted or unsubstituted $C_1$-$C_5$-alkyl, substituted or unsubstituted branched $C_1$-$C_5$-alkyl, or $R_2$ and $R_3$ form a part of a 5- to 10-membered fused or unfused ring, optionally a chiral 5- to 10-membered fused or unfused ring;

preferably $R_2$ and $R_3$ cooperatively form a part of a 5-membered ring representing 4,4,5,5-tetramethyl-[1,3,2]dioxaborolane.

(6) The process according to any one of the preceding items, wherein said catalyst is a catalyst for homogeneous catalysis.

(7) The process according to any one of the preceding items, wherein said catalyst comprises at least one ligand containing electron-rich species such as various double bonded compounds and/or free electron pair containing O, N, S, or P species.

(8) The process according to any one of the preceding items, wherein the catalyst has chirality in the ligand and/or at the transition metal atom, or the transition metal complex having chirality is formed in situ by using an achiral procatalyst comprising the transition metal together with a cocatalyst having chirality (9) The process according to any one of the preceding items, wherein the chiral components are selected from ligand(s) and/or transition metal atom(s) or transition metal catalyst formed in situ are in enantiontiopure or diastereomerically pure form, preferably at least one of said ligands has chirality, wherein said ligand(s) is/are in enantiopure or diasteriomerically pure form.

(10) The process according to any one of the preceding items, wherein the catalyst comprises ligand(s) selected from (S)-2-(1-(bis(2,6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)-P,N-ferrocene oxazoline; (R,R)-P,N-ferrocene imidazoline; benzoyl-(R,R)-P,N-ferrocene imidazoline; (R)-(+)-2,2',6,6'-tetramethoxy4,4'-bis(diphenylphosphino)-3,3'-bipyridine; (S)-2,2',6,6'-tetramethoxy-bis[di(3,5-dimethylphenyl) phosphino]-3,3'-bipyridine; (R)-4,12-bis(diphenylphosphino)-[2.2]-paracyclophane; 1-(S)—N-methyl-N-(diphenyl-phosphino)-1-[(R)-(diphenylphosphino)-ferrocenyl]ethylamine; (R)-2-(1-naphthyl)-8-diphenylphosphino-1-(S)-3,5-dioxa-4-phosphacyclohepta[2,1-1;3,4-a']di-naphthalen-4-yl)-1,2-dihydroquinoline toluene aduct; (S)-(+)-4,12-bis[di(3,5-dimethylphenyl)phosphino]-[2.2]paracyclophane; (R)-2,2'-bis (diphenyl-phosphinoamino)-5,5',6,6',7,7',8,8'-octahydro-1,1'-binaphthyl; preferably, the ligand(s) are selected from (S)-2-(1-(bis(2,6-dimethylphenyl)phosphino)-2-methylpropan-2-yl)-4-tert-butyl-4,5-dihydro-oxazole; (S)-4-tert-butyl-2-(2-(diphenylphosphino)phenyl)-4,5-dihydrooxazole; (4S,5S)-4-(2-(dicyclohexyl-phosphinooxy)-1,3-diphenylpropan-2-yl)-5-methyl-2-phenyl-4,5-dihydrooxazole, (R,R)-P,N-ferrocene oxazoline, (R,R)-P,N-ferrocene imidazoline and benzoyl-(R,R)-P,N-ferrocene imidazoline.

(11) The process according to any one of the preceding items, wherein at least one transition metal of the catalyst is selected from the group consisting of Cu, Co, Ni, Rh, Ru, Pd and Ir, preferably Rh, Ru, Pd and Ir, more preferably Ru and Ir, and in particular Ir.

(12) The process according to any one of the preceding items, wherein the catalyst is selected from the group consisting of (1,5-cyclooctadiene) (pyridine)(tricyclohexylphosphine) iridium(I) hexafluorophosphate; (1,5-cyclooctadiene)iridium(I)tetrakis[3,5-bis(trifluoromethyl)phenyl] borate (S)-2-(1-(bis(2,6-dimethylphenyl)phosphino)-2-methylpropan-2-yl)-4-tert-butyl-4,5-dihydrooxazole; (1,5-cyclooctadiene) iridium(I)tetrakis[3,5-bis(trifluoromethyl) phenyl]borate (S)-4-tert-butyl-2-(2-(diphenylphosphino) phenyl)-4,5-dihydro-oxazole; (1,5-cyclooctadiene)iridium (I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole; (1,5-cyclooctadiene)indium(I)tetrakis[3,5-bis(trifluoromethyl) phenyl]borate (R,R)-P,N-ferrocene oxazoline; (1,5-cyclooctadiene)iridium(I)tetrakis[3,5-bis(trifluoromethyl) phenyl]borate (R,R)-P,N-ferrocene imidazoline, (1,5-cyclooctadiene)iridium(I)tetrakis[3,5-bis-(trifluoromethyl) phenyl]borate benzoyl-(R,R)-P,N-ferrocene imidazoline, bis (1,5-cyclooctadiene)diiridium(I) dichloride (R)-(+)-2,2',6,6'-tetramethoxy-4,4'-bis(diphenylphosphino)-3,3'-bipyridine; bis(1,5-cyclooctadiene)diiridium(I)dichloride (S)-2,2',6,6'- tetramethoxy-bis[di(3,5-dimethylphenyl)phosphino]-3,3'-bipyridine; bis(1,5-cyclooctadiene)dirhodium (I)dichloride (S)-2,2',6,6'-tetramethoxy-bis[di(3,5-dimethylphenyl)phosphino]-3,3'-bipyridine; bis(cycloocta-1,5-diene)rhodium(I) tetrafluoroborate (R)-4,12-bis(diphenylphosphino)[2.2]-paracyclophane; benzeneruthenium(II)dichloride dimer 1-(S)—N-methyl-N-(diphenylphosphino)-1-[(R)-(diphenylphosphino)-ferrocenyl]ethylamine and bis(2-methylallyl)(1,5-cyclooctadien)ruthenium (II) (S)-(+)-4,12-bis[di(3,5-dimethylphenyl)phosphino]-[2.2]paracyclophane.

(13) The process according to any one of the preceding items, wherein the catalyst is used at a molar substrate to catalyst ratio in the range of 5:1 to 100:1, more preferably at a molar substrate to catalyst ratio in the range of 5:1 to 50:1.

(14) The process according to any one of the preceding items, wherein hydrogenation is carried out at a temperature from about 10° C. to 80° C., preferably at about 45° C. to 55° C., more preferably about 50° C.

The term "about" as used herein means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

(15) The process according to any one of the preceding items, wherein hydrogenation is carried out at a pressure of hydrogen of about 5 to 20 bar; and/or
wherein the reaction time is about 1 to 20 days, preferably about 1 to 10 days.

(16) The process according to any one of the preceding items, wherein dehalogenation occurs in less than 5 molar %, preferably in less than 3 molar %, more preferably in less than molar 1% relative to the molar amount of compound of formula VI.

(17) The process according to any one of the preceding items, wherein enantiomerically pure compound of formula VI is obtained by enantiomeric resolution applied subsequent to hydrogenation.

"Enantiomeric resolution" as employed herein means separating enantiomers by means known in the art such as chiral column chromatography or by crystallization of diastereomeric salts.

(18) The process according to any one of the preceding items, wherein a solvent for the halogenation reaction is selected from the group consisting of THF, $CH_2Cl_2$, 1,2-dichloroethane or toluene

(19) Use of a process according to any one of items (1) to (18) in a process for producing a pharmaceutically active compound.

According to this aspect of the invention, the process described in the preceding items provides for an efficient and particularly improved and more safe production of pharmaceutically active compounds, since there are substantially less byproducts in form of both dehalogenated compound of formula VI and highly corrosive and potentially toxic hydrogen halides. High yields of a desired pharmaceutically active compound are obtained in high purities, wherein less purification steps being required. Furthermore, corrosion of production facilities due to hydrogen halides is effectively reduced.

For example, X in compound VI can be valuable of its own, i.e. as a structural group in the pharmaceutical active compound. In other usefuel embodiments, X can be used as a leaving group, e.g. to readily allow $SN_2$ reactions, thereby being replaced by other structural groups as desired.

(20) Use of an iridium catalyst for hydrogenation of compounds of formula V

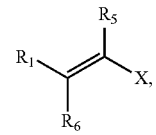

wherein
$R_1$ and $R_6$ is hydrogen, substituted or unsubstituted alkyl substituted or unsubstituted aryl, or substituted or unsubstituted aralkyl;
$R_5$ is $OR_2$, $NR_2R_3$, $SR_2$, $B(OR_2)(OR_3)$, or X" selected from F, Cl, Br, I, $OCOR_2$, $OSO_2R_2$, wherein $R_2$ and $R_3$ independently from each other represent substituted or unsubstituted alkyl, substituted or unsubstituted aryl, or substituted or unsubstituted aralkyl; or $R_2$ and $R_3$ cooperatively form a part of a 5- to 10-membered fused or unfused ring, optionally a chiral 5- to 10-membered fused or unfused ring;
X is selected from F, Cl, Br, I.

According to this aspect of the invention, a process for the use of an iridium catalyst for hydrogenation of compounds of formula V is provided, where dehalogenation, which is a common side reaction of hydrogenation of halogen alkanes, e.g. chloroalkenes, is particularly efficiently reduced to an industrially applicable level in the preparation of haloalkanes from haloalkenes.

Preferably and advantageously, in the aforementioned use of an iridium catalyst for hydrogenation of compounds of formula V, dehalogenation occurs in less than 10 molar %, more preferably in less than 5 molar %, most preferably in less than 3 molar %, in particular in less than molar 1% relative to the molar amount of hydrogenated, non-dehalogenated product obtained from the compound of formula V

(21) The use according to item (20), wherein $R_5$ is $B(OR_2)(OR_3)$.

(22) The use according to item (20) or (21), wherein X is selected from Cl, Br, I.

(23) The use according to any one of items (20) to (22), wherein $R_1$ or/and $R_6$ is/are (independently from each other) selected from hydrogen or a group consisting of substituted or unsubstituted linear $C_1$-$C_5$-alkyl, substituted or unsubstituted branched $C_1$-$C_5$-alkyl and substituted or unsubstituted $C_3$-$C_8$-cycloalkyl, preferably $R_1$ or/and $R_6$ is/are (independently from each other) selected from hydrogen or unsubstituted linear or branched $C_1$-$C_5$-alkyl, more preferably $R_1$ and/or $R_6$ is/are hydrogen or isopropyl; and/or
wherein either $R_1$ or $R_6$ is hydrogen, preferably $R_6$ is hydrogen; and/or
wherein $R_2$ and $R_3$ are selected from a group consisting of linear substituted or unsubstituted $C_1$-$C_5$-alkyl, substituted or unsubstituted branched $C_1$-$C_5$-alkyl, or $R_2$ and $R_3$ form a part of a 5- to 10-membered fused or unfused ring, optionally a chiral 5- to 10-membered fused or unfused ring;
preferably $R_2$ and $R_3$ cooperatively form a part of a 5-membered ring representing 4,4,5,5-tetramethyl-[1,3,2]dioxaborolane.

(24) The use according to any one of items (20) to 23), wherein said iridium catalyst comprises at least one ligand containing electron-rich species such as various double bonded compounds and/or free electron pair containing O, N, S, or P species.

(25) The use according to any one of items (20) to 24), wherein the iridium catalyst has chirality in the ligand and/or at the transition metal atom, or the transition metal complex having chirality is formed in situ by using an achiral procatalyst comprising the transition metal together with a cocatalyst having chirality, preferably, the chiral components selected from ligand(s) and/or transition metal atom(s) or transition metal catalyst formed in situ are in enantiontiopure or diastereomerically pure form, more preferably, at least one of said ligands has chirality, wherein said ligand(s) is/are in enantiopure or diasteriomerically pure form.

(26) The use according to any one of items (20) to (25), wherein the iridium catalyst comprises ligand(s) selected from (S)-2-(1-(bis(2,6-dimethylphenyl)phosphino)-2-methylpropan-2-yl-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)-P,N-ferrocene oxazoline; (R,R)-P,N-ferrocene imidazoline; benzoyl-(R,R)-P,N-ferrocene imidazoline; (R)-(+)-2,2',6,6'-tetramethoxy4,4'-bis(diphenylphosphino)-3,3'-bipyridine; (S)-2,2',6,6'-tetramethoxy-bis[di(3,5-dimethylphenyl) phosphino]-3,3'-bipyridine; (R)-4,12-bis(diphenylphosphino)-[2.2]-paracyclophane; 1-(S)—N-methyl-N-(diphenyl-phosphino)-1-[(R)-(diphenylphosphino)-ferrocenyl]ethylamine; (R)-2-(1-naphthyl)-8-diphenylphosphino-1-(S)-3,5-dioxa-4-phosphacyclohepta[2,1-1;3,4-a']di-naphthalen-4-yl)-1,2-dihydroquinoline toluene aduct; (S)-(+)-4,12-bis[di(3,5-dimethylphenyl)phosphino]-[2.2]paracyclophane; (R)-2,2'-bis(diphenyl-phosphinoamino)-5,5',6,6',7,7',8,8'-octahydro-1,1'-binaphthyl; preferably, the ligand(s) are selected from (S)-2-(1-(bis(2,6-dimethylphenyl)phosphino)-2-methylpropan-2-yl)-4-tert-butyl-4,5-dihydro-oxazole; (S)-4-tert-butyl-2-(2-(diphenylphosphino)phenyl)-4,5-dihydrooxazole; (4S,5S)-4-(2-(dicyclohexyl-phosphinooxy)-1,3-diphenylpropan-2-yl)-5-methyl-2-phenyl-4,5-dihydrooxazole, (R,R)-P,N-ferrocene oxazoline, (R,R)-P,N-ferrocene imidazoline and benzoyl-(R,R)-P,N-ferrocene imidazoline.

(27) The use according to any one of items (20) to (26), wherein the iridium catalyst is selected from the group consisting of (1,5-cyclooctadiene) (pyridine)(tricyclohexylphosphine) iridium(I) hexafluorophosphate; (1,5-cyclooctadiene)indium(I)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole; (1,5-cyclooctadiene)iridium(I)tetrakis[3,5-bis(trifluoromethyl)phenyl]borate (S)-4-tert-butyl-2-(2-(diphenylphosphino)phenyl)-4,5-dihydro-oxazole; (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole; (1,5-cyclooctadiene)iridium(I)tetrakis[3,5-bis(trifluoromethyl)phenyl]borate (R,R)-P,N-ferrocene oxazoline; (1,5-cyclooctadiene)iridium(1)tetrakis[3,5-bis(trifluoromethyl)phenyl]borate (R,R)-P,N-ferrocene imidazoline, (1,5-cyclooctadiene)iridium(I)tetrakis[3,5-bis-(trifluoromethyl)phenyl]borate benzoyl-(R,R)-P,N-ferrocene imidazoline, bis (1,5-cyclooctadiene)diiridium(I)dichloride (R)-(+)-2,2',6,6'-tetramethoxy-4,4'-bis(diphenylphosphino)-3,3'-bipyridine and bis(1,5-cyclooctadiene)diiridium(I)dichloride (S)-2,2',6,6'-tetramethoxy-bis[di(3,5-dimethylphenyl)phosphino]-3,3'-bipyridine.

(28) The use according to any one of items (20) to (27), wherein the iridium catalyst is used at a molar substrate to catalyst ratio in the range of 5:1 to 100:1, more preferably at a molar substrate to catalyst ratio in the range of 5:1 to 50:1.

DETAILED DESCRIPTION OF THE INVENTION

In the following, the present invention will be described in more detail by preferred embodiments and examples noting, however, that these embodiments, examples are presented for illustrative purposes only and shall not limit the invention in any way. Specifically, the following description exemplifies compounds of formulae VI and V wherein $R_5=B(OR_2)(OR_3)$ and $R_6$=hydrogen to illustrate the invention, while it can be appreciated that the concept of the invention can be accomplished likewise for structural variants of compounds of formulae VI and V wherein $R_5$ and $R_6$ are other than $B(OR_2)(OR_3)$ and hydrogen respectively. The invention therefore is not limited to the exemplified embodiments, but structural variations can be contemplated by a person skilled in the art.

Reaction Scheme 1 illustrates a preferred embodiment of the process according to the present invention for preparing an α-substituted boronic ester (VI), wherein the significant step is from compound of formula V to compound of formula VI.

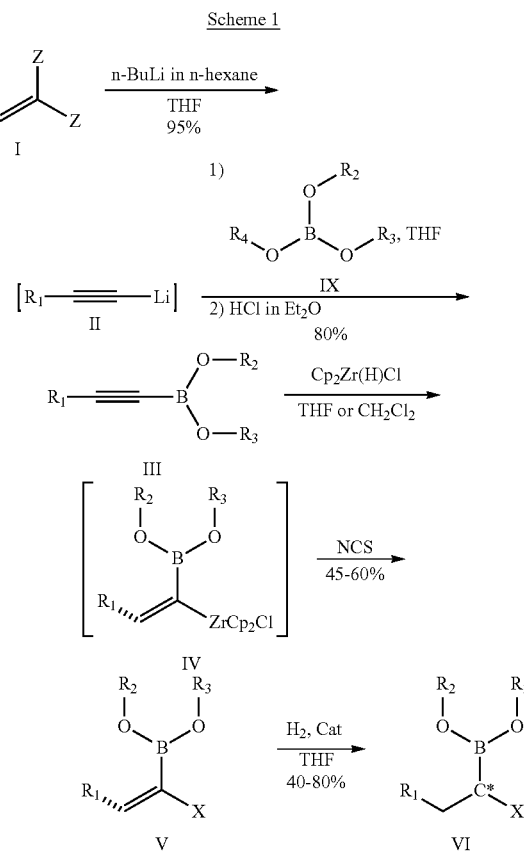

According to the preferred embodiment of Scheme 1 (wherein $R_1$, $R_2$, $R_3$, X are as defined as in the items above, and Z is Cl, Br or I), a compound of formula III is prepared by contacting a compound of formula I with a strong organometallic base, e.g. an organolithium reagent such as n-BuLi in n-hexane, to obtain a compound of formula II, which is an acetylide, in this case, since organolithium reagent is used, a lithium acetylide. Then, without isolation of compound of formula II and its respective acetylene derivate $R_1C\equiv CH$, the reaction proceeds in the same reaction vessel by adding a compound of formula IX to yield the compound of formula III. The last step of this reaction is carried out by addition of an acid such as anhydrous HCl. Both steps of the reaction, elimination and addition, to compound III are performed in organic solvent, preferably in THF.

The compound of formula I, a starting material of the synthesis presented in Scheme 1, is available; for example, it can be prepared by synthesis routes known to a person skilled in the art, as e.g. described in Tetrahedron Letters 2000, 41, 4007-4009.

Further according to the preferred embodiment illustrated by Scheme 1, a compound of formula V is prepared by subjecting a compound of formula III to hydrozirconation to obtain a compound of formula IV, which is followed by halogenation, preferably in situ halogenation. Hydrozirconation as used herein means forming organozirconocenes using $Cp_2Zr(H)Cl$ (also known as Schwartz reagent), a method well known to a person skilled in the art. Halogenation can be achieved for example by adding various halogen reagents which express positive charge on halogen, preferably N-halogenosuccinimide (e.g. N-chlorosuccinimide, NCS as illustrated in Scheme 1) in situ to a compound of formula IV to yield the compound of formula V. The reaction is carried out in organic solvent such as THF or $CH_2Cl_2$, which is later removed under reduced pressure. The reaction mixture is extracted with n-hexane and the residue is purified by chromatography.

Alternatively, halogen introduced subsequent to hydrozirconation as described above, can be optionally further converted to a moiety selected from the group consisting of OCOR' and $OSO_2R'$, wherein R' represents substituted or unsubstituted alkyl, substituted or unsubstituted aryl or substituted or unsubstituted aralkyl, by methods well known from the state of the art. For example, following a protocol of U.S. Pat. No. 4,924,026 a halogen atom, e.g. Cl (compound of formula V with X=Cl in Scheme 1), can be converted to a moiety OCOMe (compound of formula V with X=OCOMe in Scheme 1).

The hydrohalogenation of alkyne boronates via Schwartz intermediates yields de novo formed alkenes, which theoretically exist in two geometrical isomers. Based on the literature data (J. Am. Chem. Soc. 1994, 116, 10302-10303) the (E) configuration is supposedly formed predominantly. In, the light of the present invention, the determination of the configuration is not necessary, since the β carbon atom is not prochiral in view of the process of our invention.

Further according to the preferred embodiment illustrated by Scheme 1, a compound of formula VI is prepared by hydrogenation/reduction of the compound of formula V. The reaction is performed in an organic solvent, preferably THF, $CH_2Cl_2$, 1,2-dichloroethane (DCE) or toluene, in the presence of a catalyst selected from complexes comprising transition metal(s). It is suitably carried out in an autoclave under inert atmosphere.

In order that the catalyst substantially contributes to a reduced tendency of dehalogenation, it is selected from transition metal complexes wherein the transition metal is preferably selected from the group consisting of Cu, Co, Ni, Rh, Ru, Pd, Ir. More preferably, the catalyst is a transition metal-(phosphine)-complex wherein the transition metal is preferably Cu, Rh, Ru, Pd, Ir, in particular Ir. Preferably, the transition metal is complexed with at least one organic compound containing electron-rich species such as various double bonded compounds and/or free electron pair containing O, N, S, or P species as a ligand. More preferably, the transition metal catalyst has chirality in the ligand and/or at the transition metal atom, or the transition metal complex having chirality is formed in situ by using an achiral procatalyst comprising the transition metal together with a cocatalyst having chirality, such as a chiral ligand. Even more preferably, the aforementioned components having chirality are in enantiomerically or diastereomerically pure form. In particular, at least one of said ligands has chirality, wherein said ligand(s) is/are in enantiomerically or diasteriomerically pure form. Such ligands for instance may include, but are not limited to, (S)-2-(1-(bis(2,6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)-P,N-ferrocene oxazoline; (R,R)-P,N-ferrocene imidazoline; benzoyl-(R,R)-P,N-ferrocene imidazoline; (R)-(+)-2,2',6,6'-tetramethoxy-4,4'-bis(diphenylphosphino)-3,3'-bipyridine (i.e. (R)-P-Phos); (S)-2,2',6,6'-tetramethoxy-bis[di(3,5-dimethylphenyl) phosphino]-3,3'-bipyridine (i.e. (S)-Xyl-P-Phos); (R)-4,12-bis(diphenylphosphino)-[2.2]-paracyclophane (i.e. (R)-Phane-Phos); 1-(S)—N-methyl-N-(diphenylphosphino)-1-[(R)-(diphenylphosphino)-ferrocenyl]ethylamine (i.e. (S)-MeBoPhos); (R)-2-(1-naphthyl)-8-diphenyl-phosphino-1-(S)-3,5-dioxa-4-phosphacyclohepta[2,1-1;3,4-a']dinaphthalen-4-yl)-1,2-dihydroquinoline toluene aduct (i.e. (Sa,Rc)-(1-Nph)-quinaphos); (S)-(+)-4,12-bis[di(3,5-dimethylphenyl)phosphino]-[2.2]paracyclophane (i.e. (S)-XylPhanePhos); (R)-2,2'-bis(diphenyl-phosphinoamino)-5,5',6,6',7,7',8,8'-octahydro-1,1'-binaphthyl (i.e. (R)—H8-Binam-P). Preferred chiral ligands are (S)-2-(1-(bis(2,6-dimethylphenyl)phosphino)-2-methylpropan-2-yl)-4-tert-butyl-4,5-dihydro-oxazole; (S)-4-tert-butyl-2-(2-(diphenylphosphino)phenyl)-4,5-dihydrooxazole; (4S,5S)-4-(2-(dicyclohexyl-phosphinooxy)-1,3-diphenylpropan-2-yl)-5-methyl-2-phenyl-4,5-dihydrooxazole; (R,R)-P,N-ferrocene oxazoline; (R,R)-P,N-ferrocene imidazoline and benzoyl-(R,R)-P,N-ferrocene imidazoline. Some of the aforementioned ligands are exemplarily illustrated in Scheme 2 below.

Scheme 2

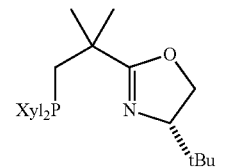

(S)-2-(1-(bis(2,6-dimethylphenyl)
phosphino)-2-methylpropan-2-yl)-
4-tert-butyl-4,5-dihydrooxazole

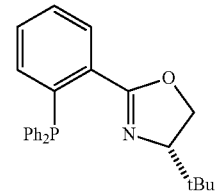

(S)-4-tert-butyl-2-(2-
(diphenylphosphino)phenyl)-
4,5-dihydrooxazole

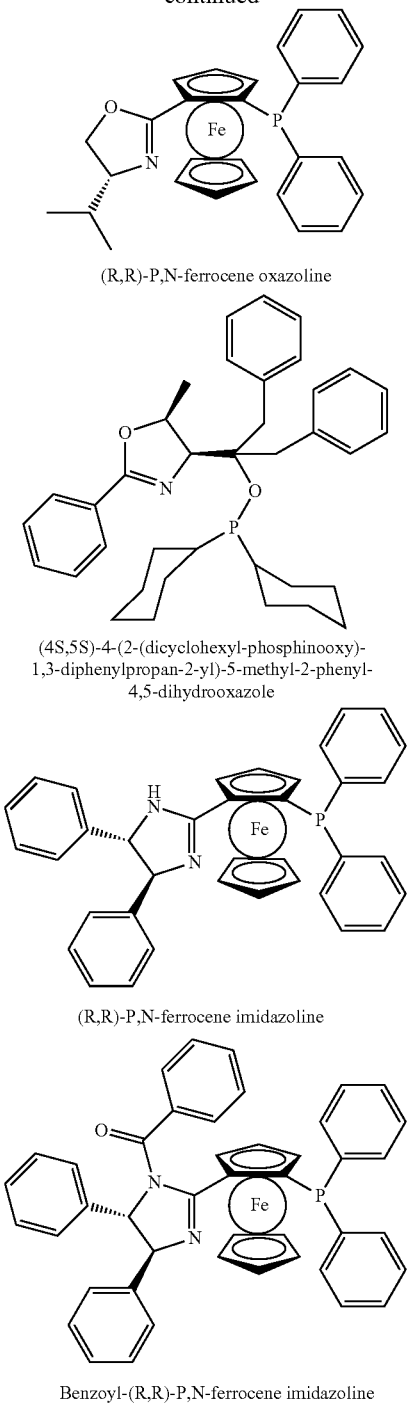

(R,R)-P,N-ferrocene oxazoline (4S,5S)-4-(2-(dicyclohexyl-phosphinooxy)-1,3-diphenylpropan-2-yl)-5-methyl-2-phenyl-4,5-dihydrooxazole (R,R)-P,N-ferrocene imidazoline Benzoyl-(R,R)-P,N-ferrocene imidazoline A non-limiting list of transition metal catalysts having chiral ligands includes (1,5-cyclooctadiene)iridium(I)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole; (1,5-cyclooctadiene) iridium(I) tetrakis[3,5-bis(trifluoromethyl) phenyl]borate (S)-4-tert-butyl-2-(2-(diphenylphosphino)phenyl)-4,5-dihydrooxazole; (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydro-oxazole; (1,5-cyclooctadiene) iridium(I)tetrakis[3,5-bis(trifluoromethyl) phenyl]borate (R,R)-P,N-ferrocene oxazoline; (1,5-cyclooctadiene)iridium(I)tetrakis[3,5-bis(trifluoromethyl)phenyl]borate (R,R)-P,N-ferrocene imidazoline; (1,5-cyclooctadiene) iridium(I)tetrakis[3,5-bis(trifluoromethyl)phenyl]borate Benzoyl-(R,R)-P,N-ferrocene imidazoline; bis(1,5-cyclooctadiene)diiridium(I)dichloride (R)-(+)-2,2',6,6'-tetramethoxy-4,4'-bis(diphenylphosphino)-3,3'-bipyridine; bis(1,5-cyclooctadiene)diiridium(I)dichloride (S)-2,2',6,6'-tetramethoxy-bis[di(3,5-dimethylphenyl)phosphino]-3,3'-bipyridine; bis(1,5-cyclooctadiene)dirhodium (I)dichloride (S)-2,2',6,6'-tetramethoxy-bis[di(3,5-dimethylphenyl)phosphino]-3,3'-bipyridine; bis(cycloocta-1,5-diene)rhodium(I) tetrafluoroborate (R)-4,12-bis(diphenylphosphino)-[2.2]-paracyclophane; benzeneruthenium(II)dichloride dimer 1-(S)—N-methyl-N-(diphenylphosphino)-1-[(R)-(diphenylphosphino)-ferrocenyl]ethylamine; bis(2-methylallyl)(1,5-cyclooctadien)ruthenium (II) (S)-(+)-4,12-bis[di(3,5-dimethylphenyl)phosphino]-[2.2]paracyclophane;

Furthermore, the complexes comprising transition metal(s) are preferably used at a molar substrate to catalyst ratio in the range of 5:1 to 100:1, more preferably at a molar substrate to catalyst ratio in the range of 5:1 to 50:1. Particularly preferred catalysts are (1,5-cyclooctadiene)(pyridine)(tricyclohexylphosphine)iridium(I) hexafluoro-phosphate; (1,5-cyclooctadiene)indium(I)tetrakis[3,5-bis(trifluoromethyl)phenyl]borate (S)-2-(1-(bis(2,6-dimethylphenyl) phosphino)-2-methylpropan-2-yl)-4-tert-butyl-4,5-dihydrooxazole, (1,5-cyclo-octadiene)iridium(I)tetrakis[3,5-bis(trifluoromethyl)phenyl]borate (S)-4-tert-butyl-2-(2-(diphenylphosphino) phenyl)-4,5-dihydrooxazole, (1,5-cyclooctadiene)iridium(I)tetrakis[3,5-bis(trifluoromethyl) phenyl]borate (4S,5S)-4-(2-(dicyclohexylphosphinooxy)-1,3-diphenylpropan-2-yl)-5-methyl-2-phenyl-4,5-dihydrooxazole, (1,5-cyclooctadiene)iridium(I)tetrakis[3,5-bis(trifluoromethyl)phenyl]borate (R,R)-P,N-ferrocene oxazoline, (1,5-cyclooctadiene)iridium(I)tetrakis[3,5-bis(trifluoromethyl)phenyl]borate (R,R)-P,N-ferrocene imidazoline and (1,5-cyclooctadiene) iridium(I)tetrakis[3,5-bis(trifluoromethyl)phenyl]borate Benzoyl-(R,R)-P,N-ferrocene imidazoline.

The compound of formula V, the Ir-catalyst and a suitable organic solvent, preferably THF, CH$_2$Cl$_2$, DCE or toluene, are placed in the autoclave under nitrogen atmosphere. The autoclave is sealed and pressurized/depressurized several times with nitrogen, preferably 3 times with about 6 bar of nitrogen, then several times with hydrogen, preferably 3 times with about 6 bar of hydrogen. The mixture is then stirred for a suitable time period, for example 1 to 20 days, preferably for about 1 to 10 days at a temperature from 10° C. to 80° C., more preferably at about 45° C. to 55° C. under about 5 to 10 bar of hydrogen. After this time period the autoclave is cooled to room temperature such as about 20° C. to 25° C. Then, the autoclave is carefully depressurized and the solution obtained is poured into a suitable vessel, preferably a round bottomed flask. The solvent is removed under reduced pressure and the residue is passed through a short column of silica gel, with suitable eluent, preferably n-hexane, to remove the catalyst. Such preferred procedure using an iridium catalyst provides for substantially reduced dehalogenation, preferably dehalogenation occurs in less than 10 molar %, more preferably in less than 5 molar %, most preferably in less than 3 molar %, in particular in less than molar 1% relative to the molar amount of compound of formula VI.

According to another embodiment of the present invention, the racemic mixture of α-(R) and α-(S) isomers of compound VI obtained in the reaction of hydrogenation of compound V, can be further separated by enantiomeric resolution in order to yield optically pure α-(R) or α-(S)-enantiomer. Since enantiomers to not differ in their scalar characteristics, enantiomeric resolution needs a chiral environment. A chiral environment for separation may be provided for example by chiral supporters in a chromatographic column or by adding enantiopure acid/base addition salts in order to form diastereomeric salts which can be separated by crystallisation. In a special case wherein the borolane part of compound of formula VI is chiral, compound of formula VI represents a diastereomer. Since diastereomers differ in their scalar characteristics, diastereomeric comounds of formula VI can be separated without providing a chiral environment, e.g by crystallization or chromatographic methods on achiral supporters.

Another preferred aspect of the invention is the use of the aforementioned hydrogenation process for producing a pharmaceutically active compound providing for a particularly improved production of pharmaceutically active compounds. Since low levels of byproducts in form of both dehalogenated compound of formula VI and highly corrosive hydrogen halides can be avoided, high yields of a desired pharmaceutically active compound are obtained in high chemical and optical purities, and less purification steps are required.

In the following, the use of the present hydrogenation process for producing a pharmaceutically active compound, here bortezomib, is further elucidated. For example, compound of formula VI can be converted into an α-amino boronic ester derivative of compound of formula VIII, as depicted in Scheme 3.

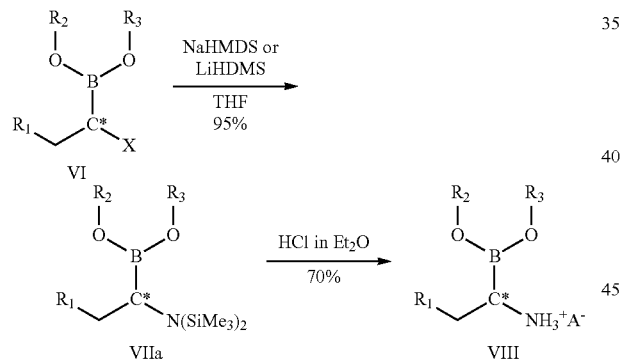

Scheme 3

Next, compound of formula VIII' (wherein $R_1$=isopropyl, $R_2$ and $R_3$=cooperatively form a part of a 5-membered ring representing 4,4,5,5-tetramethyl-[1,3,2]dioxaborolane and $A^-$=Cl$^-$) is reacted with compound of formula X in order to obtain bortezomib, as depicted in Scheme 4.

Scheme 4

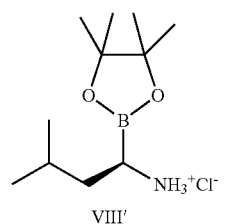

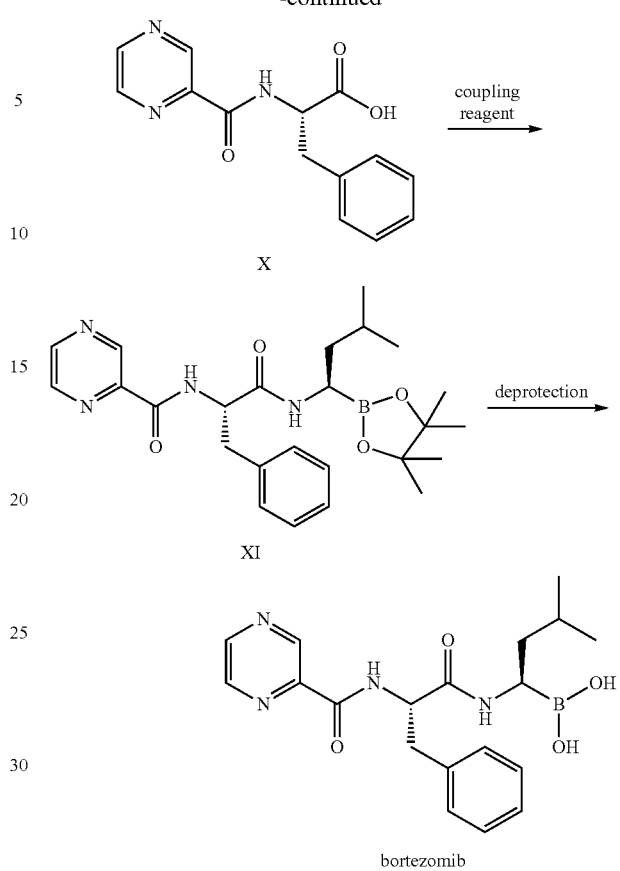

bortezomib

EXPERIMENTAL PROCEDURES

Example 1a

Synthesis of 4,4,5,5-tetramethyl-2-(3-methylbut-1-ynyl)-1,3,2-dioxaborolane (IIIa)

Scheme 5a

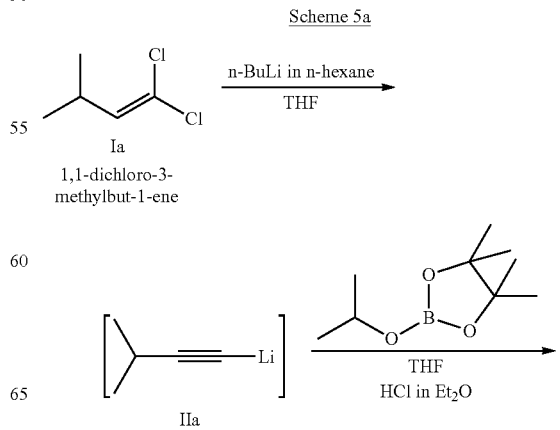

-continued

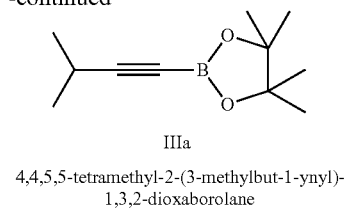

IIIa 4,4,5,5-tetramethyl-2-(3-methylbut-1-ynyl)-1,3,2-dioxaborolane

To a stirred solution of Ia (7.0 g, 50 mmol) in dry THF (25 mL) at −78° C. was added n-BuLi (1.6 M in n-hexane, 62.5 mL, 100 mmol). After being stirred for 1 hour at −78° C., the reaction mixture was warmed to room temperature and stirred for 1 hour at that temperature. Another flask was charged with 2-isopropoxy-4,4,5,5-tetramethyl-1,3,2-dioxaborolane (7.8 mL, 38 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (100 mmol) was added. Then, reaction mixture was warmed to room temperature. After removal of the precipitated LiCl by filtration and removal of solvents under reduced pressure, the residue was purified by distillation (113-115° C./7 mbar) to afford IIIa (5.9 g, 80%) as an oil.

$^1$H NMR (CDCl$_3$): δ (ppm)=1.15 (d, 6H), 1.25 (s, 12H), 2.45-2.6 (m, 1H).

$^{13}$C NMR (CDCl$_3$): δ (ppm)=21.0, 22.2, 24.5, 83.9.

Starting material Ia was prepared as described in Tetrahedron Letters 2000, 41, 4007-4009.

Example 1b

Synthesis of 2-(3,3-dimethylbut-1-ynyl)-4,4,5,5-tetramethyl-1,3,2-dioxaborolane (IIIb)

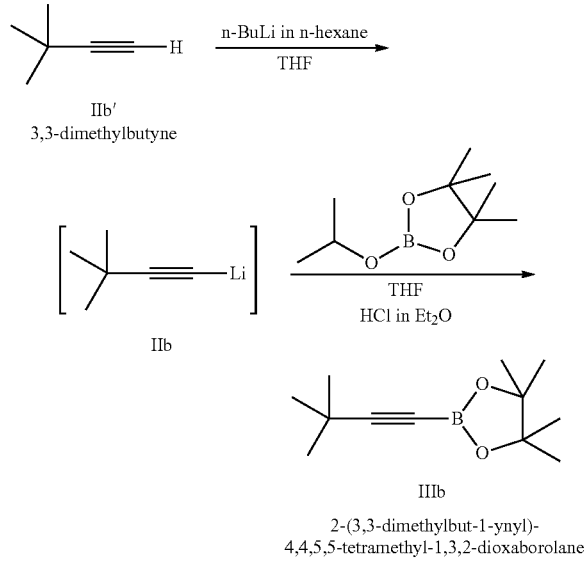

To a stirred solution of IIb' (5 mL, 40 mmol) in dry THF (25 mL) at −78° C. was added n-BuLi (2.5 M in n-hexane, 18 mL, 44 mmol). Another flask was charged with 2-isopropoxy-4,4,5,5-tetramethyl-1,3,2-dioxaborolane (8.2 mL, 40 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (44 mmol) was added. Then, reaction mixture was warmed to room temperature. After removal of the precipitated LiCl by filtration and removal of solvents under reduced pressure, the residue was purified by distillation (115-125° C./15 mbar) to afford IIIb (4.3 g, 52%) as a colourless, greasy solid.

$^1$H NMR (CDCl$_3$): δ (ppm)=1.20 (s, 9H), 1.25 (s, 12H).

$^{13}$C NMR (CDCl$_3$): δ (ppm)=24.6, 27.9, 30.4, 84.0.

Example 1c

Synthesis of 4,4,5,5-tetramethyl-2-(pent-1-ynyl)-1,3,2-dioxaborolane (IIIc)

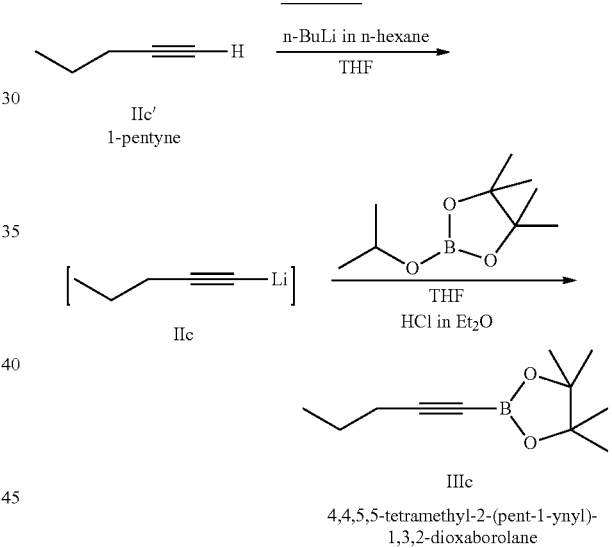

To a stirred solution of IIc' (5 mL, 51 mmol) in dry THF (25 mL) at −78° C. was added n-BuLi (2.5 M in n-hexane, 22.4 mL, 56 mmol). Another flask was charged with 2-isopropoxy-4,4,5,5-tetramethyl-1,3,2-dioxaborolane (10.4 mL, 51 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (56 mmol) was added. Then, reaction mixture was warmed to room temperature. After removal of the precipitated LiCl by filtration and removal of solvents under reduced pressure, the residue was purified by distillation (115-125° C./15 mbar) to afford IIIc (6.3 g, 64%) as an oil.

$^1$H NMR (CDCl$_3$): δ (ppm)=0.95 (t, 3H), 1.25 (s, 12H), 1.50-1.60 (m, 2H), 2.20 (t, 2H).

$^{13}$C NMR (CDCl$_3$): δ (ppm)=13.4, 21.3, 21.4, 24.45, 24.5, 83.9.

Example 1d

Synthesis of 4,4,5,5-tetramethyl-2-(phenylethynyl)-1,3,2-dioxaborolane (IIId)

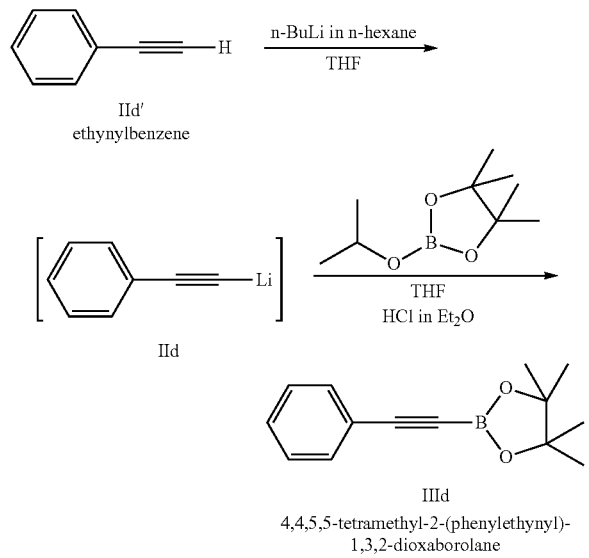

To a stirred solution of IId' (10 mL, 91 mmol) in dry THF (50 mL) at −78° C. was added n-BuLi (2.5 M in n-hexane, 40 mL, 100 mmol). Another flask was charged with 2-isopropoxy-4,4,5,5-tetramethyl-1,3,2-dioxaborolane (18.7 mL, 91 mmol) in dry THF (100 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (105 mmol) was added. Then, reaction mixture was warmed to room temperature. After removal of the precipitated LiCl by filtration and removal of solvents under reduced pressure, the residue was purified by distillation (185-200° C./15 mbar) to afford IIId (16.05 g, 76%) as a colourless oil.

$^1$H NMR (CDCl$_3$): δ (ppm)=1.32 (s, 12H), 7.26-7.36 (m, 3H), 7.52 (d, 2H).

$^{13}$C NMR (CDCl$_3$): δ (ppm)=24.6, 84.4, 121.8, 128.2, 129.3, 132.5.

Example 1e

Synthesis of 2-((4-fluorophenyl)ethyl)-4,4,5,5-tetramethyl-1,3,2-dioxaborolane (IIIe)

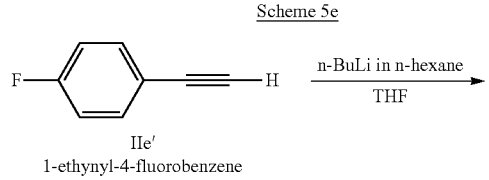

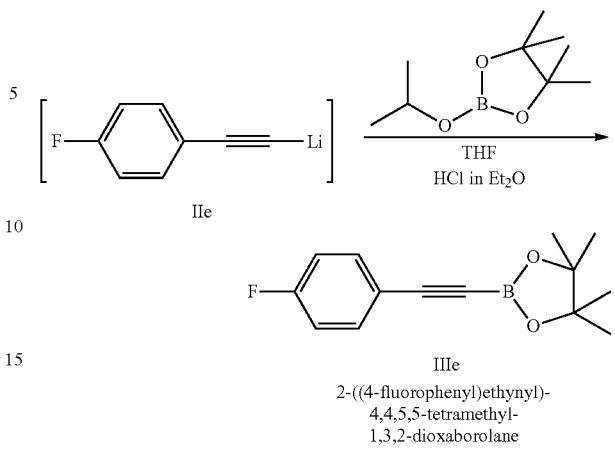

2-((4-fluorophenyl)ethynyl)-4,4,5,5-tetramethyl-1,3,2-dioxaborolane

To a stirred solution of IIe' (4.3 mL, 37 mmol) in dry THF (20 mL) at −78° C. was added n-BuLi (2.5 M in n-hexane, 16.3 mL, 41 mmol). Another flask was charged with 2-isopropoxy-4,4,5,5-tetramethyl-1,3,2-dioxaborolane (7.5 mL, 37 mmol) in dry THF (50 mL) under argon atmosphere, and the reaction mixture was cooled to −78° C. The lithium acetylide from the first flask, which was cooled to −78° C., was slowly added to the second by a double-ended needle. The mixture was stirred at −78° C. for 2 hours, after which anhydrous HCl (43 mmol) was added. Then, reaction mixture was warmed to room temperature. After removal of the precipitated LiCl by filtration and removal of solvents under reduced pressure, the residue was purified by distillation (175-185° C./15 mbar) to afford IIIe (7.2 g, 79%) as a colourless greasy solid.

$^1$H NMR (CDCl$_3$): δ (ppm)=1.32 (s, 12H), 7.0 (t, 2H), 7.52 (t, 2H).

$^{13}$C NMR (CDCl$_3$): δ (ppm)=24.6, 84.4, 115.5, 115.8, 117.9, 134.5, 134.6, 161.8, 164.3.

Example 2

Synthesis of 2-(1-chloro-3-methylbut-1-enyl)-4,4,5-tetramethyl-1,3,2-dioxaboro-lane (Va)

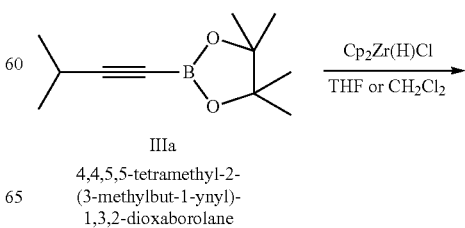

IIIa
4,4,5,5-tetramethyl-2-(3-methylbut-1-ynyl)-1,3,2-dioxaborolane

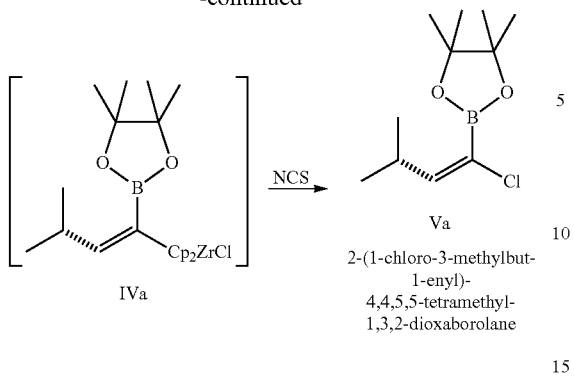

Va
2-(1-chloro-3-methylbut-1-enyl)-4,4,5,5-tetramethyl-1,3,2-dioxaborolane

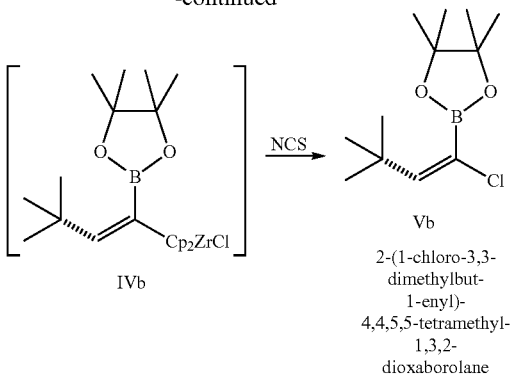

Vb
2-(1-chloro-3,3-dimethylbut-1-enyl)-4,4,5,5-tetramethyl-1,3,2-dioxaborolane a) With THF as a Solvent A suspension of $Cp_2Zr(H)Cl$ (7.3 g, 27 mmol) in dry THF (55 mL) was stirred at room temperature under argon atmosphere. Then, a 48 mL of 0.5 M solution of IIIa (24 mmol) in dry THF was added. The reaction mixture was stirred for 1 hour, resulting in a clear orange solution. Addition of N-chlorosuccinimide (3.6 g, 27 mmol) in situ led to the discharge of the colour of the solution. The solvent was removed under reduced pressure, and n-hexane (5×20 mL) was added to extract the reaction mixture. After removal of solvent under reduced pressure, the residure was purified by chromatography (mobile phase: n-hexane/MTBE=9.5/0.5) to afford Va (2.5 g, 45%) as an oil.

b) With $CH_2Cl_2$ as a Solvent

A suspension of $Cp_2Zr(H)Cl$ (7.3 g, 27 mmol) in dry $CH_2Cl_2$ (55 mL) was stirred at room temperature under argon atmosphere. Then, a 48 mL of 0.5 M solution of IIIa (24 mmol) in $CH_2Cl_2$ was added. The reaction mixture was stirred for 1 hour, resulting in a clear orange solution. Addition of N-chlorosuccinimide (3.6 g, 27 mmol) in situ led to the discharge of the colour of the solution. The solvent was removed under reduced pressure, and n-hexane (5×20 mL) was added to extract the reaction mixture. After removal of solvent under reduced pressure, the residure was purified by chromatography (mobile phase: n-hexane/MTBE=9.5/0.5) to afford Va (3.3 g, 60%) as an oil.

$^1H$ NMR ($CDCl_3$): δ (ppm)=0.95 (d, 6H), 1.25 (s, 12H), 2.95-3.05 (m, 1H), 6.35 (d, 1H).

$^{13}C$ NMR ($CDCl_3$): δ (ppm)=22.8, 24.6, 29.5, 84.2, 156.2.

Example 2c

Synthesis of 2-(1-chloro-3,3-dimethyl-1-enyl)-4,4,5,5-tetramethyl-1,3,2-dioxaborolane (Vb)

Scheme 6b

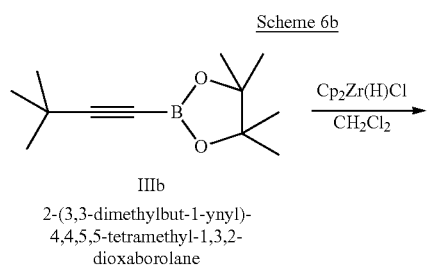

IIIb
2-(3,3-dimethylbut-1-ynyl)-4,4,5,5-tetramethyl-1,3,2-dioxaborolane

A suspension of $Cp_2Zr(H)Cl$ (6.8 g, 25 mmol) in dry $CH_2Cl_2$ (50 mL) was stirred at room temperature under argon atmosphere. Then, a 43 mL of 0.5 M solution of IIIb (23 mmol) in $CH_2Cl_2$ was added. The reaction mixture was stirred for 1 hour, resulting in a clear orange solution. Addition of N-chlorosuccinimide (3.3 g, 25 mmol) in situ led to the discharge of the colour of the solution. The solvent was removed under reduced pressure, and n-hexane (5×20 mL) was added to extract the reaction mixture. After removal of solvent under reduced pressure, the residure was purified by chromatography (mobile phase: n-hexane/MTBE=9.5/0.5) to afford Vb (1.7 g, 30%) as an oil.

$^1H$ NMR ($CDCl_3$): δ (ppm)=1.1 (s, 9H), 1.3 (s, 12H), 6.3 (s, 1H).

$^{13}C$ NMR ($CDCl_3$): δ (ppm)=24.4, 29.7, 34.8, 84.4, 152.1.

Example 2d

Synthesis of 2-(1-chloro-pent-1-enyl)-4,4,5,5-tetramethyl-1,3,2-dioxaborolane (Vc)

Scheme 6c

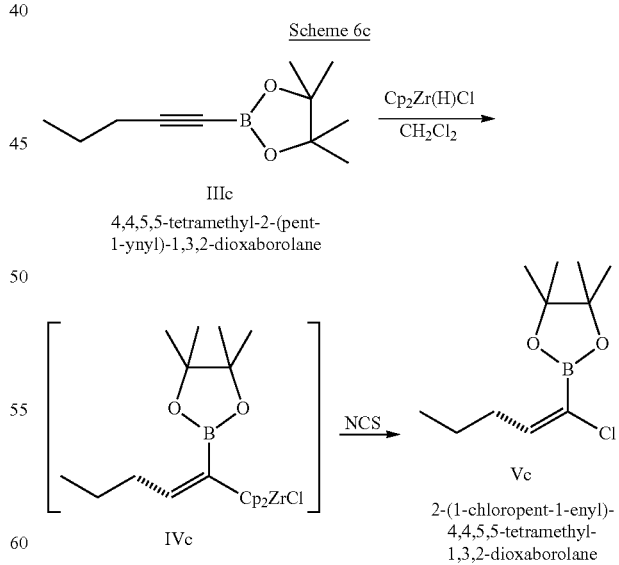

IIIc
4,4,5,5-tetramethyl-2-(pent-1-ynyl)-1,3,2-dioxaborolane

Vc
2-(1-chloropent-1-enyl)-4,4,5,5-tetramethyl-1,3,2-dioxaborolane

A suspension of $Cp_2Zr(H)Cl$ (7.3 g, 27 mmol) in dry $CH_2Cl_2$ (54 mL) was stirred at room temperature under argon atmosphere. Then, a 47 mL of 0.5 M solution of IIIc (24.5 mmol) in $CH_2Cl_2$ was added. The reaction mixture was stirred for 1 hour, resulting in a clear orange solution. Addition of N-chlorosuccinimide (3.6 g, 27 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Vc (2.95 g, 48%) as an oil.

$^1$H NMR (CDCl$_3$): δ (*ppm*)=0.9 (t, 3H), 1.25 (d, 12H), 1.35-1.50 (m, 2H), 2.3 (q, 2H), 6.5 (t, 1H).

$^{13}$C NMR (CDCl$_3$): δ (*ppm*)=13.4, 22.4, 24.6, 31.9, 84.2, 149.4.

Example 2e

Synthesis of 2-(1-chloro-2-phenylvinyl)-4,4,5,5-tetramethyl-1,3,2-dioxaborolane (Vd)

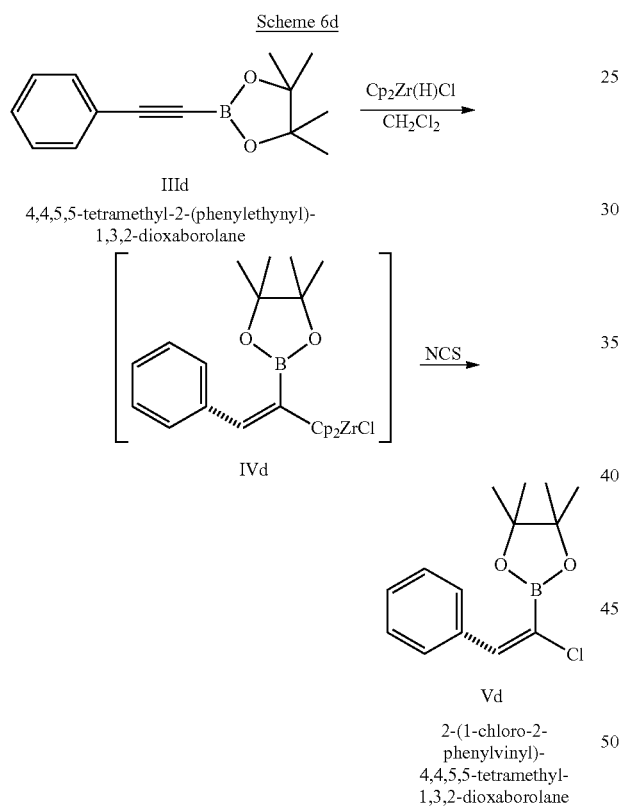

A suspension of Cp$_2$Zr(H)Cl (6.94 g, 26 mmol) in dry CH$_2$Cl$_2$ (51 mL) was stirred at room temperature under argon atmosphere. Then, a 42 mL of 0.5 M solution of IIId (21.3 mmol) in CH$_2$Cl$_2$ was added. The reaction mixture was stirred for 1 hour, resulting in a clear orange solution. Addition of N-chlorosuccinimide (3.5 g, 26 mmol) in situ led to the discharge of the colour of the solution. The solvent was removed under reduced pressure, and n-hexane (5×30 mL) was added to extract the reaction mixture. After removal of solvent under reduced pressure, the residue was purified by chromatography (mobile phase: n-hexane/MTBE=9.5/0.5) to afford Vd (2.5 g, 45%) as an oil.

$^1$H NMR (CDCl$_3$): δ (*ppm*)=1.33 (s, 12H), 7.24-7.39 (m, 6H).

$^{13}$C NMR (CDCl$_3$): δ (*ppm*)=24.5, 84.7, 128.1, 128.17, 128.2, 135.5, 143.2.

Example 2f

Synthesis of 2-(1-chloro-2-(4-fluorophenyl)vinyl)-4,4,5,5-tetramethyl-1,3,2-dioxaborolane (Ve)

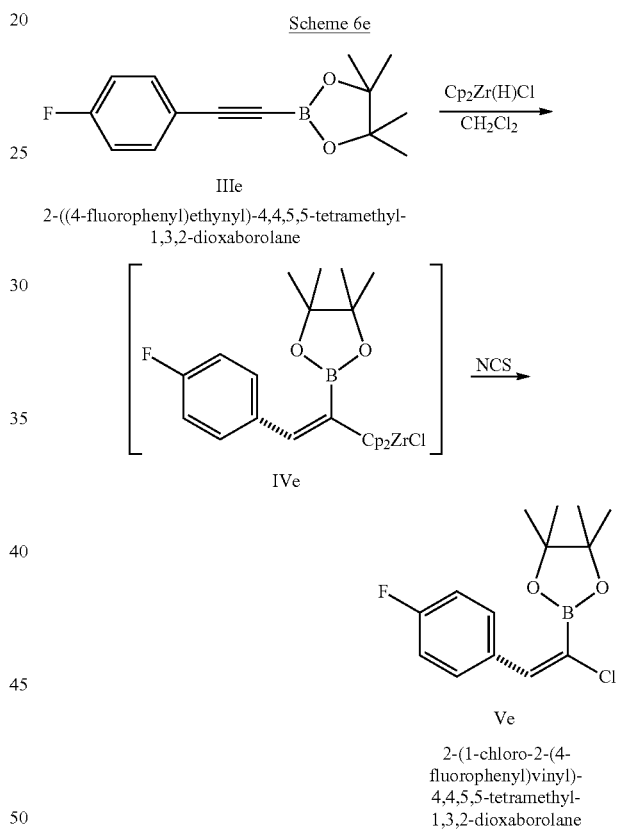

A suspension of Cp$_2$Zr(H)Cl (4.0 g, 14.8 mmol) in dry CH$_2$Cl$_2$ (35 mL) was stirred at room temperature under argon atmosphere. Then, a 27 mL of 0.5 M solution of IIIe (13.5 mmol) in CH$_2$Cl$_2$ was added. The reaction mixture was stirred for 1 hour, resulting in a clear orange solution. Addition of N-chlorosuccinimide (1.97 g, 14.8 mmol) in situ led to the discharge of the colour of the solution. The solvent was removed under reduced pressure, and n-hexane (5×20 mL) was added to extract the reaction mixture. After removal of solvent under reduced pressure, the residue was purified by chromatography (mobile phase: n-hexane/MTBE=9.5/0.5) to afford Ve (1.1 g, 30%) as an oil.

$^1$ NMR (CDCl$_3$): δ (*ppm*)=1.32 (s, 12H), 7.0 (t, 2H), 7.32-7.39 (m, 3H).

$^{13}$C NMR (CDCl$_3$): δ (ppm)=24.5, 84.8, 115.0, 115.2, 130.2, 131.6, 131.7, 142.6, 161.5, 163.9.

Example 3a

Synthesis of 2-(1-chloro-3-methylbutyl)-4,4,5,5-tetramethyl-1,3,2-dioxaborolane (VIa)

Scheme 7a

Va
2-(1-chloro-3-methylbut-1-enyl)-
4,4,5,5-tetramethyl-1,3,2-dioxaborolane

VIa
2-(1-chloro-3-methylbutyl)-
4,4,5,5-tetramethyl-1,3,2-dioxaborolane

Meaning of the abbreviation used:
Cat*a) = (1,5-cyclo-octadiene)(pyridine)(tricyclohexylphosphine)iridium(I) hexafluorophosphate The 75 mL stainless steel autoclave was flushed with nitrogen. The substrate Va (1.15 g, 5.0 mmol), the (1,5-cyclo-octadiene)(pyridine)(tricyclohexylphosphine)iridium(I) hexafluorophosphate (80.5 mg, 0.1 mmol) and dry THF (30 mL) were quickly placed in the autoclave under nitrogen atmosphere. The autoclave was sealed and pressurized/depressurized first 3 times with 6 bar of nitrogen, then 3 times with 6 bar of hydrogen. The mixture was stirred for 10 days at 50° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane) to removed catalyst. The product VIa (0.84 g, 80%) was carried over into next step without further purification.

$^1$H NMR (CDCl$_3$): δ (ppm)=0.9 (m, 6H), 1.3 (s, 1H), 1.45-1.5 (m, 1H), 1.75-1.85 (m, 1H), 1.87-1.95 (m, 1H), 3.5-3.6 (m, 1H).

$^{13}$C NMR (CDCl$_3$): δ (ppm)=22.8, 24.5, 25.5, 31.6, 42.5, 84.3.

Example 3b-d

Synthesis of (R)- or (S)-2-(1-chloro-3-methylbutyl)-4,4,5,5-tetramethyl-1,3,2-dioxaborolane (R- or S-VIa)

Scheme 7b

Va
2-(1-chloro-3-methylbut-1-enyl)-
4,4,5,5-tetramethyl-1,3,2-dioxaborolane

R- or S-VIa
(R)- or (S)-2-(1-chloro-3-methylbutyl)-
4,4,5,5-tetramethyl-1,3,2-dioxaborolane Cat*
b) [Ir(cod)Cl]$_2$, (R)-P-Phos
c) [Rh(cod)Cl]$_2$, (S)-Xyl-P-Phos
d) [Ir(cod)Cl]$_2$, (S)-Xyl-P-Phos Meaning of the abbreviations used for the Catalysts:
Cat*b = Bis(1,5-cyclooctadiene) diiridium(I)dichloride (R)-(+)-2,2',6,6'-Tetramethoxy 4,4'-bis(diphenylphosphino)-3,3'-bipyridine;
Cat*c = Bis(1,5-cyclooctadiene) dirhodium (I)dichloride (S)-2,2',6,6'-Tetramethoxy-bis[di(3,5-dimethylphenyl)phosphino]-3,3'-bipyridine;
Cat*d = Bis(1,5-cyclooctadiene) diiridium(I)dichloride (S)-2,2',6,6'-Tetramethoxy-bis[di(3,5-dimethylphenyl)phosphino]-3,3'-bipyridine;

The 75 mL stainless steel autoclave is flushed with nitrogen. The substrate Va (1.15 g, 5.0 mmol), the appropriate catalyst (Cat*b-d; 80.5 mg, 0.1 mmol) and dry THF (30 mL) are quickly placed in the autoclave under nitrogen atmosphere. The autoclave is sealed and pressurized/depressurized first 3 times with 6 bar of nitrogen, then 3 times with 6 bar of hydrogen. The mixture is stirred for 10 days at 50° C. under 10 bar of hydrogen. Once the autoclave is cooled to room temperature, the autoclave is carefully depressurized, the solution is poured into a round bottomed flask. The solvent is removed under reduced pressure and the residue is passed through a short column of silica gel (eluent=n-hexane) to remove the catalyst. The product R- or S-VIa is carried over into next step without further purification. In case the catalysis does not provide for sufficient enantiomeric excess, e.g. enantiomeric excess is less than about 99%, enantiomeric resolution can be applied prior to carrying out the next reaction step.

Example 3e-h

Synthesis of (R)- or (S)-2-(1-chloro-3-methylbutyl)-4,4,5,5-tetramethyl-1,3,2-dioxaborolane (R- or S-VIa)

Scheme 7c

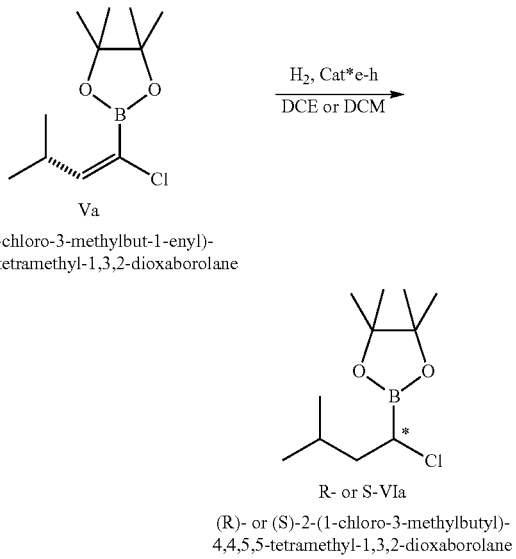

Va
2-(1-chloro-3-methylbut-1-enyl)-4,4,5,5-tetramethyl-1,3,2-dioxaborolane

R- or S-VIa
(R)- or (S)-2-(1-chloro-3-methylbutyl)-4,4,5,5-tetramethyl-1,3,2-dioxaborolane Cat*e: [Ir(cod)Lig-1]BAr$_F$
Cat*f: [Ir(cod)Lig-2]BAr$_F$
Cat*g: [Ir(cod)Lig-3]BAr$_F$
Cat*h: [Ir(cod)Lig-4]BAr$_F$ Meaning of the abbreviations used:
Cat*e = (1,5-Cyclooctadiene)iridium(I)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole
Cat*f = (1,5-Cyclooctadiene)iridium(I)tetrakis[3,5-bis(trifluoromethyl)phenyl]borate (S)-4-tert-butyl-2-(2-(diphenylphosphino)phenyl)-4,5-dihydrooxazole
Cat*g = (1,5-Cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole
Cat*h = (1,5-Cyclooctadiene)iridium(I)tetrakis[3,5-bis(trifluoromethyl)phenyl]borate (R,R)-P,N-ferrocene oxazoline
cod = 1,5-cyclooctadiene
BAr$_F$ = 3,5-bis(trifluoromethyl)phenyl]borate
DCE = 1,2-dichloroethane
DCM = dichloromethane The 15 mL stainless steel autoclave was flushed with nitrogen. The substrate Va (0.5 mmol), the appropriate catalyst (Cat*e-f: 0.01 mmol; Cat*g: 0.02 mmol) and DCE (3 mL) were quickly placed in the autoclave under nitrogen atmosphere. The autoclave was sealed and pressurized/depressurized first 3 times with 6 bar of nitrogen, then 3 times with 6 bar of hydrogen. The mixture was stirred for 20 hours at 50° C. under 20 bar of hydrogen. Once the autoclave was cooled to room temperature, the autoclave was carefully depressurized, the solution was poured into a round bottomed flask. The solvent was removed under reduced pressure and the residue was passed through a short column of silica gel (eluent=n-hexane) to remove the catalyst. The product R- or S-VIa was carried over into next step without further purification.

Parameters of the enantioselective hydrogenation of Va by using catalysts Cat*e-h are presented as follows:

| | Cat./Metal precursor | Solvent | S/C ratio | Enantiomeric excess (e.e.) [% GC] | Configuration |
|---|---|---|---|---|---|
| 1 | Cat*e | DCE | 50 | 86 | S |
| 2 | Cat*f | DCE | 50 | 58 | S |
| 3 | Cat*g | DCE | 25 | 71 | R |
| 4 | Cat*h | DCE | 50 | 67 | R |

DCE = 1,2-dichloroethane

Enantiomeric excess was determined by gas chromatography method using GC instrument with flame ionization detector. The column used was Supelco Astec A-TA with dimensions 30 m×0.25 mm×0.12 μm. The injector used was split/splitless, split ratio 30:1, T=250° C. GC conditions: volume of injection=1.0 μL; carrier gas=Helium, constant flow rate 1.5 mL/min; FID temperature=250° C.; Temperature gradient for analytical step=70° C. (66 min) to 130° C. (8 min) at 15° C./min; Temperature gradient for cooling step=130° C. (0 min) to 70° C. (0.1 min) at −15° C./min; Total run time=78 min (82 min with cooling). Retention times of R-VIa and S-VIa were approximately 61 and 64 min, respectively.

Example 3i

Synthesis of (S)-2-(1-chloro-3-methylbutyl)-4,4,5,5-tetramethyl-1,3,2-dioxaborolane (S-VIa)

Scheme 7d

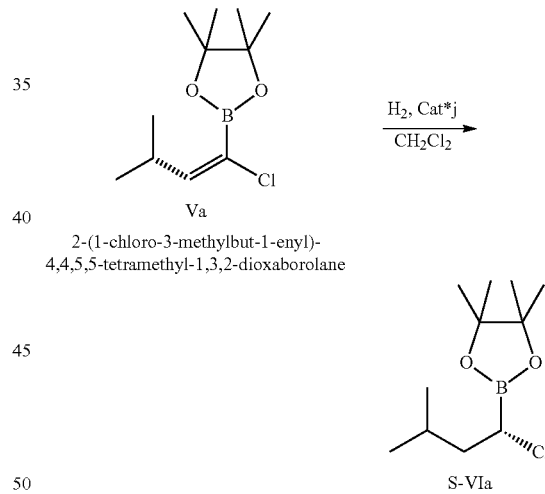

Va
2-(1-chloro-3-methylbut-1-enyl)-4,4,5,5-tetramethyl-1,3,2-dioxaborolane

S-VIa
(S)-2-(1-chloro-3-methylbutyl)-4,4,5,5-tetramethyl-1,3,2-dioxaborolane

Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (169 mg, 0.17 mmol) was placed in the autoclave under nitrogen atmosphere. The autoclave was sealed and pressurized/depressurized 3 times with 5 bar of nitrogen followed by addition of Va (1.0 g, 4.34 mmol). The system was purged with nitrogen five times and then dry CH$_2$Cl$_2$ (25 mL) was added. The system was purged five more times with nitrogen and ten times with hydrogen. The mixture was stirred for 2 days at 50° C. under 5 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product S-VIa (0.66 g, 66%, 93% ee) was carried over into next step without further purification.

The ee was established using a chiral GC under the following conditions: Column: Chrompack Capillary Column CP-Chirasil-Dex CB, 25 m×0.25 mm×0.25 µm; Injector: split ratio 30, T=250° C.; Carrier gas: helium, constant flow rate 1.5 ml/min; Detector, T=250° C.; Temperature gradient: 60° C. for 40 min, increase 0.5° C./min until 90° C., hold 2 min, decrease 15° C./min until 60° C., hold 1 min; Total runtime: 105 min. Retention times: Va: 83.4 min; R-VIa: 93.7 min; S-VIb: 94.8 min.

Example 3j

Synthesis of 2-(1-chloro-3,3-dimethylbutyl)-4,4,5,5-tetramethyl-1,3,2-dioxaborolane (VIb)

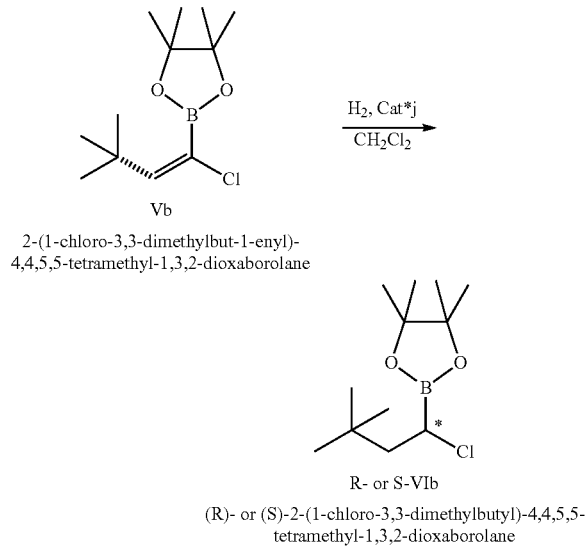

Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (567 mg, 0.57 mmol) was placed in the autoclave under nitrogen atmosphere. The autoclave was sealed and pressurized/depressurized 3 times with 5 bar of nitrogen followed by addition of Vb (1.0 g, 4.1 mmol). The system was purged with nitrogen five times and then dry $CH_2Cl_2$ (25 mL) was added. The system was purged five more times with nitrogen and ten times with hydrogen. The mixture was stirred for 2 days at 50° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=nhexane:EtOAc=9:1) to removed catalyst. The product R- or S-VIb (0.7 g, 67%, 93% ee (e2)) was carried over into next step without further purification.

The ee was established using a chiral GC under the following conditions: Column: Chrompack Capillary Column CP-Chirasil-Dex CB, 25 m×0.25 mm×0.25 µm; Injector: split ratio 30, T=250° C.; Carrier gas: helium, constant flow rate 1.0 ml/min; Detector, T=90° C.; Total run time: 60 min. Retention times: e1-VIb: 52.9 min; e2-VIb: 53.9 min; Vb: 54.7 min.

$^1$H-NMR (CDCl$_3$): δ (ppm)=0.95 (s, 9H), 1.30 (s, 12H), 1.77 (dd, 1H), 1.98 (dd, 1H), 3.47 (dd, H).
$^{13}$C-NMR (CDCl$_3$): δ (ppm)=24.5, 29.6, 31.3, 48.0, 84.2.

Example 3k

Synthesis of 2-(1-chloro-pentyl)-4,4,5,5-tetramethyl-1,3,2-dioxaborolane (VIc)

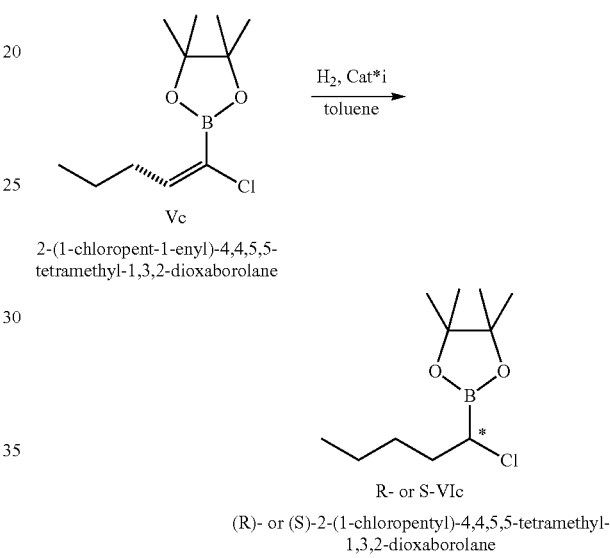

Meaning of the abbreviations used:
Cat*i = (1,5-Cyclooctadiene)iridium(I)tetrakis[3,5-bis(trifluoromethyl)phenyl]borate (R,R)-P,N-ferrocene imidazoline The 75 mL stainless steel autoclave was flushed with nitrogen. The catalyst Cat*i (183 mg, 0.2 mmol) was placed in the autoclave under nitrogen atmosphere. The autoclave was sealed and pressurized/depressurized 3 times with 5 bar of nitrogen followed by addition of Vc (1.2 g, 5 mmol). The system was purged with nitrogen five times and then dry toluene (30 mL) was added. The system was purged five more times with nitrogen and ten times with hydrogen. The mixture was stirred for 2 days at 80° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product R- or S-VIc (0.48 g, 40%, 85% ee (e2)) was carried over into next step without further purification.

The ee was established using a chiral GC under the following conditions: Column: Chrompack Capillary Column CP-Chirasil-Dex CB, 25 m×0.25 mm×0.25 µm; Injector: split ratio 30, T=250° C.; Carrier gas: helium, constant flow rate 1.5 ml/min; Detector, T=250° C.; Temperature: 100° C. for 30 min; Total run time: 30 min. Retention times: Vc: 20.0 min; e1-VIc: 21.5 min; e2-VIc: 22.4 min.

$^1$H-NMR (CDCl$_3$): δ (ppm)=0.92 (t, 3H), 1.30 (s, 12H), 1.36 (m, 3H), 1.48 (m, 1H), 1.83 (m, 2H), 3.42 (dd, 1H).

$^{13}$C-NMR (CDCl$_3$): δ (ppm)=14.0, 22.2, 24.6, 29.5, 33.8, 84.3.

Example 3l

Synthesis of 2-(1-chloro-2-phenylethyl)-4,4,5,5-tetramethyl-1,3,2-dioxaborolane (VId)

Scheme 7g

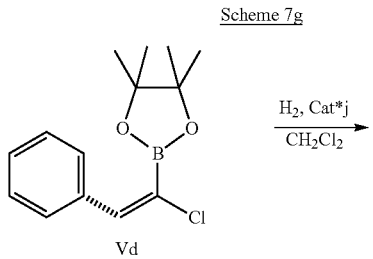

Vd
2-(1-chloro-2-phenylvinyl)-4,4,5,5-tetramethyl-1,3,2-dioxaborolane

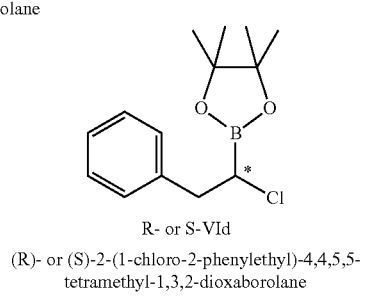

R- or S-VId
(R)- or (S)-2-(1-chloro-2-phenylethyl)-4,4,5,5-tetramethyl-1,3,2-dioxaborolane Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (490 mg, 0.49 mol) was placed in the autoclave under nitrogen atmosphere. The autoclave was sealed and pressurized/depressurized 3 times with 5 bar of nitrogen followed by addition of Vd (1.3 g, 4.9 mmol). The system was purged with nitrogen five times and then dry CH$_2$Cl$_2$ (30 mL) was added. The system was purged five more times with nitrogen and ten times with hydrogen. The mixture was stirred for 2 days at 50° C. under 10 bar of hydrogen. Once the autoclave had cooled to room temperature, the autoclave was carefully depressurized, the solution was poured into a round bottomed flask. The solvent was removed under reduced pressure and the residue was passed through a short column of silica, gel (eluent=n-hexane:EtOAc=9:1) to removed catalyst. The product R- or S-VId (0.65 g, 50%, 90% ee (e2)) was carried over into next step without further purification.

The ee was established using a chiral GC under the following conditions: Column: Chrompack Capillary Column CP-Chirasil-Dex CB, 25 m×0.25 mm×0.25 µm; Injector: split ratio 30, T=250° C.; Carrier gas: helium, constant flow rate 1.5 ml/min; Detector, T=250° C.; Temperature 110° C.; Total run time: 120 min. Retention times: e1-VId: 103.9 min, e2-VId: 106.7 min, Vd: 113.5 min.

$^1$H-NMR (CDCl$_3$) δ (ppm)=1.25 (s, 6H), 1.27 (s, 6H), 3.12 (dd, 1H), 3.21 (dd, 1H), 3.63 (t, 1H), 7.29 (m, 5H).

$^{13}$C-NMR (CDCl$_3$): δ (ppm)=24.5, 24.6, 40.3, 84.5, 126.8, 128.4, 129.2, 138.4 ppm.

Example 3m

Synthesis of 2-(1-chloro-2-(4-fluorophenypethyl)-4,4,5,5-tetramethyl-1,3,2-dioxaborolane (VIe)

Scheme 7h

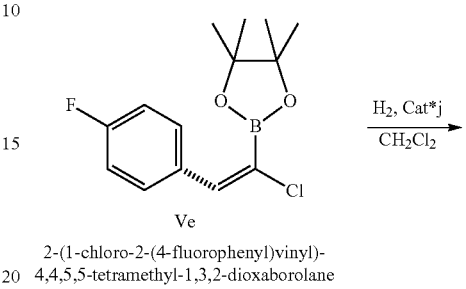

Ve
2-(1-chloro-2-(4-fluorophenyl)vinyl)-4,4,5,5-tetramethyl-1,3,2-dioxaborolane

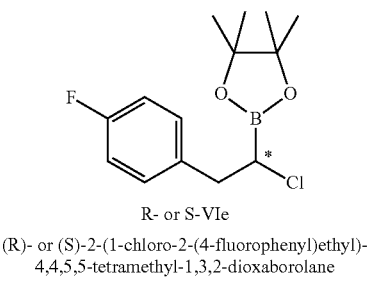

R- or S-VIe
(R)- or (S)-2-(1-chloro-2-(4-fluorophenyl)ethyl)-4,4,5,5-tetramethyl-1,3,2-dioxaborolane Meaning of the abbreviations used:
Cat*j = (1,5-Cyclooctadiene)iridium(I)tetrakis[3,5-bis(trifluoromethyl)phenyl]borate benzoyl-(R,R)-P,N-ferrocene imidazoline The 75 mL stainless steel autoclave was flushed with nitrogen. The catalyst Cat*j (350 mg, 0.35 mmol) was placed in the autoclave under nitrogen atmosphere. The autoclave was sealed and pressurized/depressurized 3 times with 5 bar of nitrogen followed by addition of Ve (1.0 g, 3.5 mmol). The system was purged with nitrogen five times and then dry CH$_2$Cl$_2$ (21 mL) was added. The system was purged five more times with nitrogen and ten times with hydrogen. The mixture was stirred for 2 days at 50° C. under 5 bar of hydrogen. Once the autoclave had cooled to room temperature, the autoclave was carefully depressurized, the solution was poured into a round bottomed flask. The solvent was removed under reduced pressure and the residue was passed through a short column of silica gel (eluent=n-hexane:EtOAc=9:1) to removed catalyst. The product R- or S-VIe (0.6 g, 60%, 89% ee (e2)) was carried over into next step without further purification.

The ee was established using a chiral GC under the following conditions: Column: Chrompack Capillary Column CP-Chirasil-Dex CB, 25 m×0.25 mm×0.25 µm; Injector: split ratio 30, T=250° C.; Carrier gas: helium, constant flow rate 1.5 ml/min; Detector, T=250° C.; Temperature 110° C.; Total run time: 120 min. Retention times: Ve+e1-VIe: 109.2 min; e2-VIe: 112.0 min.

$^1$H-NMR (CDCl$_3$): δ (ppm)=1.25 (s, 6H), 1.26 (s, 6H), 3.08 (dd, 1H), 3.16 (dd, 1H), 3.58 (t, 1H), 7.00 (t, 2H), 7.24 (dd, 2H).

$^{13}$C-NMR (CDCl$_3$): δ (ppm)=24.5, 24.6, 39.4, 84.6, 115.1, 130.7, 134.0, 161.9.

Example 4a

Synthesis of 3-methyl-1-(4,4,5,5-tetramethyl-1,3,2-dioxaborolan-2-yl)butan-1-amine hydrochloride (leucine boronate hydrochloride, VIIIa)

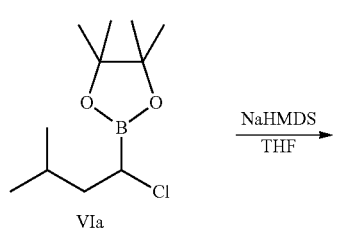

$^1$H NMR (CDCl$_3$): δ (ppm)=0.9 (d, 6H), 1.25 (s, 12H), 1.55-1.65 (m, 1H), 1.7-1.8 (m, 1H), 1.82-1.9 (m, 1H), 2.85-2.95 (m, 1H), 8.2 (s, 3H).

$^{13}$C NMR (CDCl$_3$): δ (ppm)=22.4, 22.4, 24.6, 24.9, 25.0, 38.5, 84.9.

Example 4b

Synthesis of (R)-3-methyl-1-(4,4,5,5-tetramethyl-1,3,2-dioxaborolan-2-yl)butan-1-amine hydrochloride (R-VIIIa)

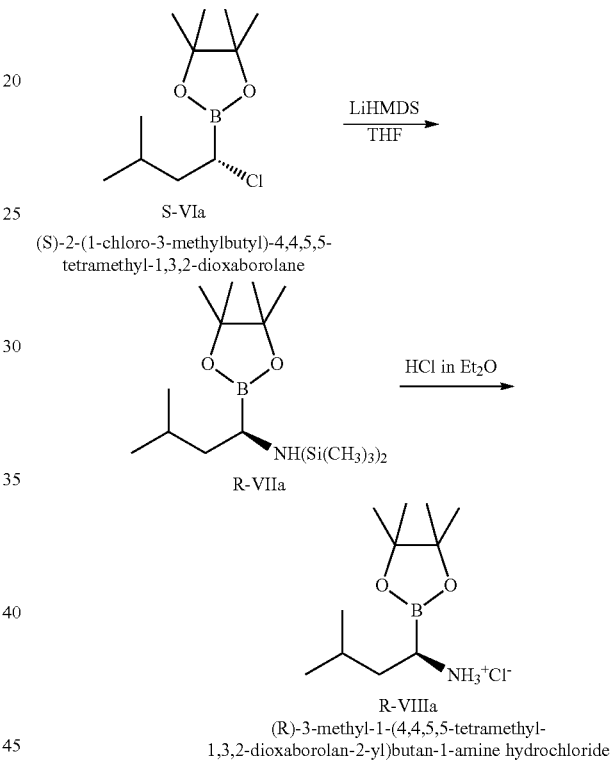

To a solution of NaHMDS (1M in THF, 3.8 mL, 3.8 mmol) in dry THF (8 mL) at −35° C. under argon atmosphere was added VIa (0.88 g, 3.8 mmol)dissolved in 8 mL dry THF. The solution was warmed to room temperature and stirred for 5 hours. The reaction mixture was evaporated to dryness. The residue was dissolved in 10 mL of n-heptane, washed with 8 mL H$_2$O and 4 mL saturated aqueous solution of NaCl. The organic phases was dried over MgSO$_4$, filtrated and evaporated to dryness. To a solution of the resulting residue taken up in n-heptane (20 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford VIIIa (0.63 g, 70%) as a white solid.

Under argon atmosphere a solution of LiHMDS (1 M in THF, 2.5 mL, 2.5 mmol) was placed in a flask and cooled at −20° C. S-VIa (0.58 g, 2.5 mmol, example 3e) was dissolved in 5 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL H$_2$O and 2 mL saturated aqueous solution of NaCl. The organic phases was dried over MgSO$_4$, filtrated and evaporated to dryness. To a solution of the resulting residue taken up in n-heptane (7 mL), anhydrous HCl (4 eq, solution in Et$_2$O) was added at −60° C. under argon atmosphere. Then, reaction mixture was warmed to room temperature. The precipitating solid was isolated from reaction mixture by filtration and washed with Et$_2$O to afford R-VIIIa (0.33 g, 56%, 92.5% ee) as a white solid.

Example 4c

Synthesis of 3,3-dimethyl-1-(4,4,5,5-tetramethyl-1,3,2-dioxaborolan-2-yl)butan-1-amine hydrochloride (VIIIb)

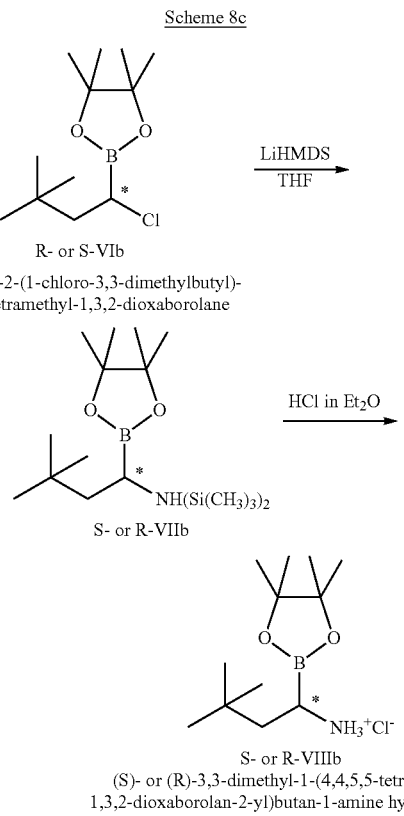

Scheme 8c

R- or S-VIb
(R)- or (S)-2-(1-chloro-3,3-dimethylbutyl)-4,4,5,5-tetramethyl-1,3,2-dioxaborolane S- or R-VIIb S- or R-VIIIb
(S)- or (R)-3,3-dimethyl-1-(4,4,5,5-tetramethyl-1,3,2-dioxaborolan-2-yl)butan-1-amine hydrochloride Under argon atmosphere a solution of LiHMDS (1M in THF, 1.9 mL, 1.9 mmol) was placed in a flask and cooled at −20° C. R- or S-VIb (0.47 g, 1.9 mmol) was dissolved in 4 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL $H_2O$ and 2 mL saturated aqueous solution of NaCl. The organic phases was dried over $MgSO_4$, filtrated and evaporated to dryness. To a solution of the resulting residue taken up in n-heptane (5 mL), anhydrous HCl (4 eq, solution in $Et_2O$) was added at −60° C. under argon atmosphere. Then, reaction mixture was warmed to room temperature. The precipitating solid was isolated from reaction mixture by filtration and washed with $Et_2O$ to afford S- or R-VIIIb (0.25 g, 50%) as a white solid.

$^1$H NMR (CDCl$_3$): δ (*ppm*)=0.98 (s, 9H), 1.32 (s, 12H), 1.73-1.88 (m, 2H), 2.88 (m, 1H), 8.18 (s, 3H).

$^{13}$C NMR (CDCl$_3$): δ (*ppm*)=24.8, 25.0, 29.7, 30.5, 43.8, 85.0.

Example 4d

Synthesis of 1-(4,4,5,5-tetramethyl-1,3,2-dioxaborolan-2-yl)pentan-1-amine hydrochloride (VIIIc)

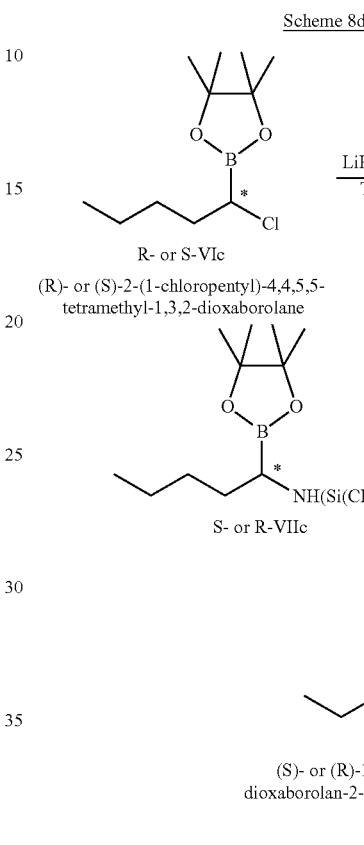

Scheme 8d

R- or S-VIc
(R)- or (S)-2-(1-chloropentyl)-4,4,5,5-tetramethyl-1,3,2-dioxaborolane S- or R-VIIc S- or R-VIIIc
(S)- or (R)-1-(4,4,5,5-tetramethyl-1,3,2-dioxaborolan-2-yl)pentan-1-amine hydrochloride Under argon atmosphere a solution of LiHMDS (1 M in THF, 1.9 mL, 1.9 mmol) was placed in a flask and cooled at −20° C. R- or S-VIc (0.47 g, 1.9 mmol) was dissolved in 4 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL $H_2O$ and 2 mL saturated aqueous solution of NaCl. The organic phases was dried over $MgSO_4$, filtrated and evaporated to dryness. To a solution of the resulting residue taken up in n-heptane (5 mL), anhydrous HCl (4 eq, solution in $Et_2O$) was added at −60° C. under argon atmosphere. Then, reaction mixture was warmed to room temperature. The precipitating solid was isolated from reaction mixture by filtration and washed with $Et_2O$ to afford S- or R-VIIIc (0.25 g, 50%) as a white solid.

$^1$H NMR (CDCl$_3$): δ (*ppm*)=0.88 (t, 3H), 1.29 (s, 12H), 1.31-1.55 (m, 4H), 1.77-1.90 (m, 2H), 2.84-2.94 (m, 1H), 8.16 (s, 3H).

$^{13}$C NMR (CDCl$_3$): δ (*ppm*)=13.8, 22.3, 24.6, 24.9, 28.5, 29.2, 37.5, 85.0.

Example 4e

Synthesis of 2-phenyl-1-(4,4,5,5-tetramethyl-1,3,2-dioxaborolan-2-yl)ethanamine hydrochloride (VIIId)

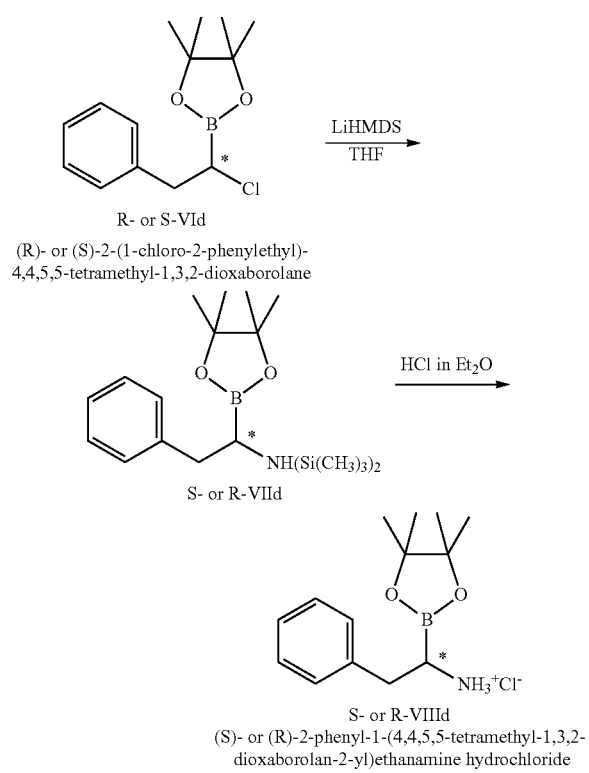

Under argon atmosphere a solution of LiHMDS (1M in THF, 2.36 mL, 2.36 mmol) was placed in a flask and cooled at −20° C. R- or S-VId (0.6 g, 2.36 mmol) was dissolved in 5 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL $H_2O$ and 2 mL saturated aqueous solution of NaCl. The organic phases was dried over $MgSO_4$, filtrated and evaporated to dryness. To a solution of the resulting residue taken up in n-heptane (5 mL), anhydrous HCl (4 eq, solution in $Et_2O$) was added at −60° C. under argon atmosphere. Then, reaction mixture was warmed to room temperature. The precipitating solid was isolated from reaction mixture by filtration and washed with $Et_2O$ to afford S- or R-VIIId (0.33 g, 50%) as a white solid.

$^1$H NMR ($CDCl_3$): δ (ppm)=1.24 (s, 12H), 3.24 (s, 3H), 7.21-7.41 (m, 5H), 8.22 (s, 3H).

$^{13}$C NMR ($CDCl_3$): δ (ppm)=24.7, 24.9, 35.4, 85.2, 105.0, 127.2, 128.7, 129.6, 136.4.

Example 4f

Synthesis of 2-(4-fluorophenyl)-1-(4,4,5,5-tetramethyl-1,3,2-dioxaborolan-2-yl)ethanamine hydrochloride (VIIIe)

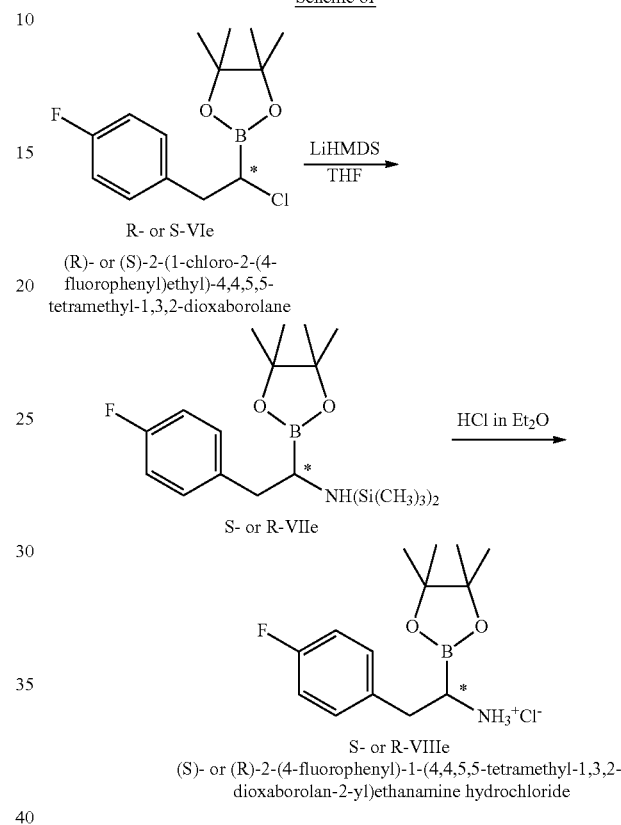

Under argon atmosphere a solution of LiHMDS (1 M in THF, 2.36 mL, 2.36 mmol) was placed in a flask and cooled at −20° C. R- or S-VIe (0.6 g, 2.36 mmol) was dissolved in 5 mL dry THF and added to the LiHMDS solution at −20° C. The mixture was stirred for 1 hour at −20° C. The reaction mixture was warmed to the room temperature and evaporated to dryness. The residue was dissolved in 5 mL of n-heptane, washed with 5 mL $H_2O$ and 2 mL saturated aqueous solution of NaCl. The organic phases was dried over $MgSO_4$, filtrated and evaporated to dryness. To a solution of the resulting residue taken up in n-heptane (5 mL), anhydrous HCl (4 eq, solution in $Et_2O$) was added at −60° C. under argon atmosphere. Then, reaction mixture was warmed to room temperature. The precipitating solid was isolated from reaction mixture by filtration and washed with $Et_2O$ to afford S- or R-VIIIe (0.33 g, 50%) as a white solid.

$^1$H NMR ($CDCl_3$): δ (ppm)=1.29 (s, 12H), 3.15-3.28 (m, 3H), 7.0 (t, 2H), 7.37 (t, 2H), 8.19 (s, 3H).

$^{13}$C NMR ($CDCl_3$): δ (ppm)=24.7, 24.9, 85.33, 115.4, 115.7, 131.2, 131.3, 132.2, 160.9, 163.3.

Example 5a

Preparation of catalysts Cat*b-d: The appropriate phosphine ligand (1.1 eq) and the metal precursor (1.0 eq) are stirred in dry THF under nitrogen atmosphere for 30 min at room temperature. The solvent is removed by evaporation and the solid is purified by flash column chromatography using hexane/CH$_2$Cl$_2$ 1/1 to afford Cat*b-d.

Example 5b

Catalysts Cat*e-g can be prepared as described in *Adv. Synth. Catal.*, 2001, 343, 450-454: To a two-necked flask fitted with condenser is added chiral P,N-ligand (Lig-1-Lig-3; 2 eq), [Ir(cod)Cl]$_2$ (1 eq) and CH$_2$Cl$_2$. The mixture is heated under nitrogen atmosphere to reflux for 1 hour. After the mixture is cooled to room temperature, Na[BAr$_F$] (3 eq) is added followed by H$_2$O, and the resulting two-phase mixture is stirred vigorously for 10 min. The layers are separated, and the aqueous layer extracted with further portions of CH$_2$Cl$_2$ (2×). The combined organic extracts are washed with H$_2$O and evaporated. The residue is taken up in EtOH and crystallized by slow addition of H$_2$O to give appropriate catalyst.

Example 5c

Catalyst Cat*i Having the Structural Formula was prepared following the synthetic sequence detailed in Scheme 9a. Starting from commercially available ferrocenyl carboxylic acid, the oxazoline ring was installed in two steps (a, b) following the protocol described in *Tetrahedron Asymmetry* 1996, 7, 1419-1430 and *J. Org. Chem.* 1996, 61, 4937-4943. The addition of the diphenyl phosphine (step c) was also carried out following above mention procedures. In order to build the imidazoline ring from the corresponding oxazoline (PL-4), the procedure described in the patent aplication U.S. 2007/0244319 A1 was followed. The Ir complex was then prepared according to the general protocol described by Pfaltz for the synthesis of P,N—Ir catalysts, *Adv. Synth. CataL* 2001, 343, 450-454.

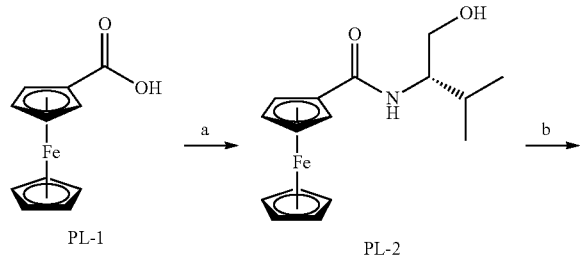

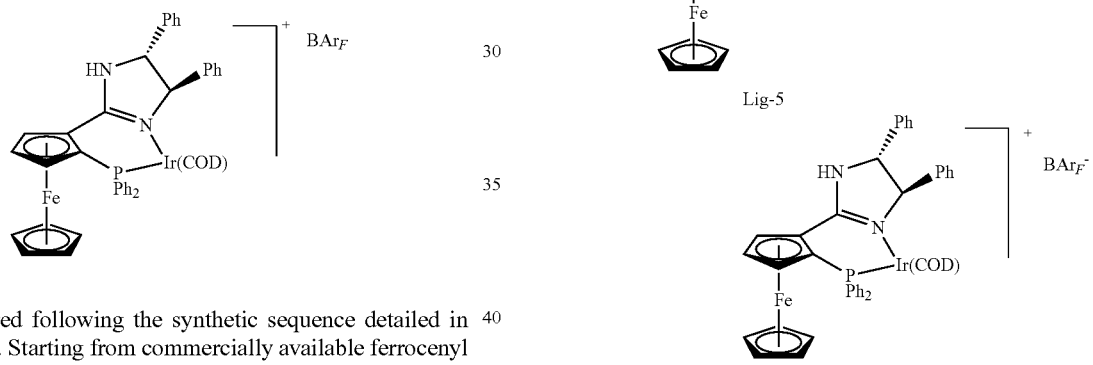

a) (COCl)$_2$, CH$_2$Cl$_2$, room temperature, 2 h; then (L)-(+)-valinol, Et$_3$N, CH$_2$Cl$_2$, room temperature, 16 h, 77% yield; b) TsCl, Et$_3$N, DMAP, CH$_2$Cl$_2$, 0° C. for 1.5 h and then room temperature for 16 h, 98% yield; c) TMEDA, BuLi, hexane, -78° C., 2 h; then Ph$_2$PCl, room temperature, 15 min, 70% yield; d) (R,R)-DPEN, CH$_3$SO$_3$H, IPA, 85° C., 40 h, 94% yield; e) [Ir(COD)Cl]$_2$, CH$_2$Cl$_2$, 50° C., 1 h; then NaBAr$_F$, H$_2$O, rt, 15 min, 87% yield.

Lig-5: In a previously dried Schlenk tube, PL-4 (1.0 g, 2.08 mmol) and (R,R)-DPEN (2.2 g, 10.24 mmol, 5.0 eq) were dissolved in dry IPA (25 mL) under nitrogen. Methanesulfonic acid (202 µL, 3.12 mmol, 1.5 eq) was added and seven cycles of vacuum and nitrogen purge were performed. The resulting solution was stirred at 85° C. for 40 h. After cooling to room temperature, the solvent was removed under vacuum. The crude obtained was purified by column chromatography using a mixture of EtOAc/hexane 1/1. Lig-5 was isolated (1.15 g, 1.96 mmol, 94% yield) as an orange solid.

$^1$H-NMR (CDCl$_3$, 400 MHz) δ=3.83 (s, 1H), 4.28 (s, 5H), 4.56 (m, 1H), 4.78 (s, 2H), 5.38 (s, 1H), 7.36 (m, 18H), 7.59 (m, 2H) ppm.

$^{13}$C-NMR (CDCl$_3$, 100 MHz) δ=60.42, 70.79, 71.57, 72.69, 73.92, 76.46 (d, J$_{C,P}$=10.1 Hz), 127.14, 128.39 (d, J$_{C/P}$=3.0 Hz), 128.49 (d, J$_{C/P}$=6.0 Hz), 128.62, 129.61, 132.51 (d, J$_{C,P}$=18.1 Hz), 135.09 (d, J$_{C,P}$=20.1 Hz), 136.07 (d, J$_{C,P}$=8.0 Hz), 138.18 (d, J$_{C,P}$=8.0 Hz), 164.46 ppm.

$^{31}$P-NMR (CDCl$_3$, 162 MHz) δ=−20.17 ppm.

Cat*i: In a previously dried Schlenk tube, Lig-5 (250 mg, 0.427 mmol) and [Ir(COD)Cl]$_2$ (149 mg, 0.222 mmol, 0.52 eq) were dissolved in dry CH$_2$Cl$_2$ (6 mL) under nitrogen and the resulting solution was stirred at 50° C. for 1 h. After cooling to room temperature, sodium tetrakis[3,5-bis(trifluoromethyl)phenyl]borate (567 mg, 0.640 mmol, 1.5 eq) was added, followed by 6 mL of water and the resulting two-phase mixture was stirred vigorously for 15 min. The layers were separated, the aqueous phase extracted with CH$_2$Cl$_2$ and the combined organic extracts evaporated under vacuum. The crude obtained was purified by flash column chromatography using hexane/CH$_2$Cl$_2$ 1/1 to afford Cat*i (650 mg, 0.371, 87% yield) as an orange solid.

$^1$H-NMR (CDCl$_3$, 400 MHz) δ=1.28 (m, 2H), 1.55 (m, 1H), 2.02 (m, 3H), 2.29 (m, 1H), 2.41 (m, 1H), 2.73 (m, 1H), 3.14 (m, 1H), 4.43 (d, J=4.0 Hz, 1H), 4.60 (s, 1H), 4.63 (s, 5H), 4.70 (m, 2H), 4.81 (d, J=5.2 Hz, 1H), 4.86 (t, J=2.4 Hz, 1H), 4.98 (s, 1H), 5.95 (s, 1H), 6.54 (d, J=7.2 Hz, 2H), 7.07 (t, J=7.2 Hz, 2H), 7.20 (m, 4H), 7.39 (m, 15H), 7.51 (m, 1H), 7.63 (s, 9H) ppm.

$^{31}$P-NMR (CDCl$_3$, 162 MHz) δ=9.42 ppm.

HRMS (+ESI) calcd for C$_{45}$H$_{43}$FeIrN$_2$P: 891.2107. found: 891.2137.

Example 5d

Catalyst Cat*j Having the Structural Formula

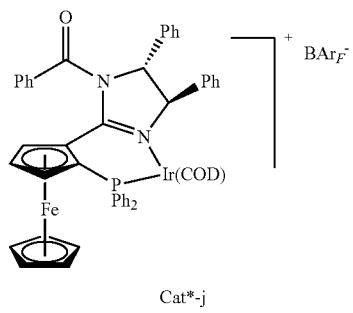

Cat*-j was prepared from the common precursor Lig-5 used for the synthesis of catalyst Cat*i (as described in Example 5c) by protecting initially the NH group in the imidazoline ring with a benzoyl group and forming next the corresponding Ir complex (Scheme 9b).

Scheme 9b

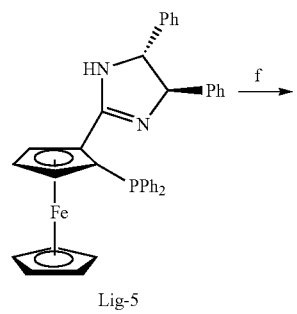

Lig-5

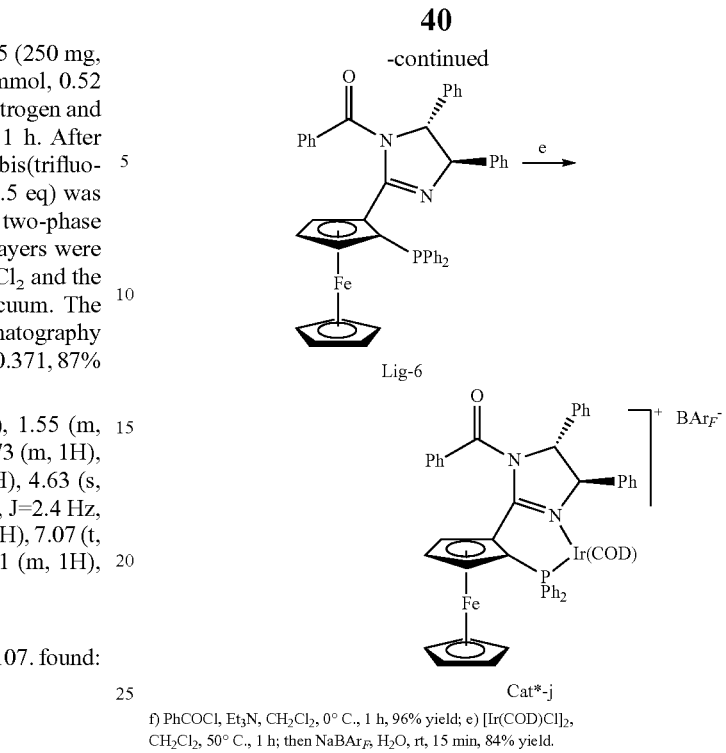

Lig-6

Cat*-j f) PhCOCl, Et$_3$N, CH$_2$Cl$_2$, 0° C., 1 h, 96% yield; e) [Ir(COD)Cl]$_2$, CH$_2$Cl$_2$, 50° C., 1 h; then NaBAr$_F$, H$_2$O, rt, 15 min, 84% yield.

Lig-6: In a previously dried Schlenk tube, Lig-5 (350 mg, 0.597 mmol) was dissolved in dry CH$_2$Cl$_2$ (7 mL) under nitrogen and then cooled to 0° C. Triethylamine (125 μL, 0.896 mmol, 1.5 eq.) and benzoyl chloride (76 μL, 0.657 mmol, 1.1 eq.) were added and the reaction mixture was stirred at 0° C. for 1 h. The reaction was worked up by removing the solvent under vacuum. The resulting crude was purified by flash column chromatography using a mixture EtOAc/hexane 1/4. The protected ligand Lig-6 was isolated as an orange solid (400 mg, 0.576, 96% yield).

$^1$H-NMR (CDCl$_3$, 400 MHz) δ=3.80 (s, 1H), 4.26 (s, 5H), 4.29 (s, 1H), 4.78 (s, 1H), 4.85 (s, 1H), 5.22 (s, 1H), 6.66 (d, J=8.4 Hz, 2H), 6.96 (t, J=7.6 Hz, 2H), 7.09 (t, J=7.6 Hz, 1H), 7.20 (t, J=7.2 Hz, 2H), 7.30 (t, J=7.6 Hz, 2H), 7.41 (m, 7H), 7.54 (m, 9H) ppm.

$^{31}$P-NMR (CDCl$_3$, 162 MHz) δ=−19.90 ppm.

Cat*j: In a previously dried Schlenk tube, Lig-6 (400 mg, 0.576 mmol) and [Ir(COD)Cl]$_2$ (201 mg, 0.299 mmol, 0.52 eq) were dissolved in dry CH$_2$Cl$_2$ (7 mL) under nitrogen and the resulting solution was stirred at 50° C. for 1 h. After cooling to room temperature, sodium tetrakis[3,5-bis(trifluoromethyl)phenyl]borate (766 mg, 0.864 mmol, 1.5 eq) was added, followed by 7 mL of water and the resulting two-phase mixture was stirred vigorously for 15 min. The layers were separated, the aqueous phase extracted with CH$_2$Cl$_2$ and the combined organic extracts evaporated under vacuum. The crude obtained was purified by flash column chromatography using hexane/CH$_2$Cl$_2$ 1/1 to afford Cat*j (896 mg, 0.482, 84% yield) as a dark red solid.

$^1$H-NMR (CDCl$_3$, 400 MHz) δ=1.40 (m, 2H), 1.76 (m, 1H), 2.07 (m, 1H), 2.31 (m, 4H), 3.08 (m, 1H), 3.43 (m, 1H), 4.38 (m, 1H), 4.67 (s, 5H), 4.70 (m, 1H), 4.85 (m, 2H), 4.89 (s, 1H), 4.92 (t, J=3.2 Hz, 1H), 5.10 (s, 1H), 6.64 (d, J=6.8 Hz, 2H), 7.14 (m, 4H), 7.27 (m, 2H), 7.32 (m, 1H), 7.43 (m, 1H), 7.53 (m, 15H), 7.67 (m, 2H), 7.75 (s, 10H) ppm.

$^{31}$P-NMR (CDCl$_3$, 162 MHz) δ=9.71 ppm.

HRMS (+ESI) calcd for C$_{52}$H$_{47}$FeIrN$_2$PO: 995.2438. found: 995.2399.

The invention claimed is:
1. A process for preparing a compound of formula VI

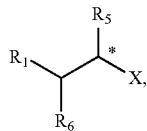

wherein
R$_1$ and R$_6$ is hydrogen, substituted or unsubstituted alkyl substituted or unsubstituted aryl, or substituted or unsubstituted aralkyl;
R$_5$ is B(OR$_2$)(OR$_3$);
wherein R$_2$ and R$_3$ independently from each other represent substituted or unsubstituted alkyl, substituted or unsubstituted aryl, or substituted or unsubstituted aralkyl; or R$_2$ and R$_3$ cooperatively form a part of a 5- to 10-membered fused or unfused ring, optionally a chiral 5- to 10-membered fused or unfused ring;
X is selected from Cl, Br, I; and
* indicates a chiral center;
by hydrogenation of a compound of formula V

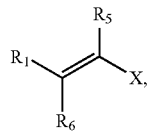

wherein R$_1$, R$_5$, R$_6$ and X are as defined above;
wherein hydrogenation is conducted in the presence of a catalyst selected from complexes comprising at least one transition metal, and said catalyst is used at a molar substrate to catalyst ratio in the range of 5:1 to 100:1, and wherein dehalogenation occurs in less than 10 molar % relative to the molar amount of the compound of formula VI.

2. The process according to claim 1, wherein R$_1$ or/and R$_6$ is/are (independently from each other) selected from hydrogen or a group consisting of substituted or unsubstituted linear C$_1$-C$_5$-alkyl, substituted or unsubstituted branched C$_1$-C$_5$-alkyl and substituted or unsubstituted C$_3$-C$_8$-cycloalkyl, preferably R$_1$ or/and R$_6$ is/are (independently from each other) selected from hydrogen or unsubstituted linear or branched C$_1$-C$_5$-alkyl, more preferably R$_1$ and/or R$_6$ is/are hydrogen or isopropyl; and/or wherein either R$_1$ or R$_6$ is hydrogen, preferably R$_6$ is hydrogen; and/or wherein R$_2$ and R$_3$ are selected from a group consisting of linear substituted or unsubstituted C$_1$-C$_5$-alkyl, substituted or unsubstituted branched C$_1$-C$_5$-alkyl, or R$_2$ and R$_3$ form a part of a 5- to 10-membered fused or unfused ring, optionally a chiral 5- to 10-membered fused or unfused ring; wherein R$_2$ and R$_3$ cooperatively form a part of a 5-membered ring representing 4,4,5,5-tetramethyl-[1,3,2]dioxaborolane.

3. The process according to claim 1, wherein said catalyst is a catalyst for homogeneous catalysis; and/or
wherein said the catalyst comprises at least one ligand containing electron-rich species such as various double bonded compounds and/or free electron pair containing O, N, S, or P species.

4. The process according to claim 1, wherein the catalyst has chirality in the ligand and/or at the transition metal atom, or the transition metal complex having chirality is formed in situ by using an achiral procatalyst comprising the transition metal together with a cocatalyst having chirality, preferably, the chiral components selected from ligand(s) and/or transition metal atom(s) or transition metal catalyst formed in situ are in enantiontiopure or diastereomerically pure form, more preferably, at least one of said ligands has chirality, wherein said ligand(s) is/are in enantiopure or diasteriomerically pure form.

5. The process according to claim 1, wherein the catalyst comprises ligand(s) selected from (S)-2-(1-(bis(2,6-dimethylphenyl)phosphino)-2-methylpropan-2-yl)-4-tert-butyl-4,5-dihydrooxazole; (S)-4-tert-butyl-2-(2-(diphenylphosphino)phenyl)-4,5-dihydrooxazole; (4S,5S)-4-(2-(dicyclohexylphosphinooxy)-1,3-diphenylpropan-2-yl)-5-methyl-2-phenyl-4,5-dihydrooxazole; (R,R)-P,N-ferrocene oxazoline; (R,R)-P,N-ferrocene imidazoline; Benzoyl-(R,R)-P,N-ferrocene imidazoline; (R)-(+)-2,2',6,6'-tetramethoxy-4,4'-bis(diphenylphosphino)-3,3'-bipyridine; (S)-2,2',6,6'-tetramethoxy-bis[di(3,5-dimethylphenyl) phosphino]-3,3'-bipyridine; (R)-4,12-bis(diphenylphosphino)-[2.2]-paracyclophane; 1-(S)—N-methyl-N-(diphenyl-phosphino)-1-[(R)-(diphenylphosphino)-ferrocenyl]ethylamine; (R)-2-(1-naphthyl)-8-diphenylphosphino-1-(S)-3,5-dioxa-4-phosphacyclohepta[2,1-1;3,4-a']di-naphthalen-4-yl)-1,2-dihydroquinoline toluene adduct; (S)-(+)-4,12-bis[di(3,5-dimethylphenyl)phosphino]-[2.2]paracyclophane; (R)-2,2'-bis(diphenyl-phosphinoamino)-5,5',6,6',7,7',8,8'-octahydro-1,1'-binaphthyl; preferably, the ligand(s) are selected from (S)-2-(1-(bis(2,6-dimethylphenyl)phosphino)-2-methylpropan-2-yl)-4-tert-butyl-4,5-dihydro-oxazole; (S)-4-tert-butyl-2-(2-(diphenylphosphino)phenyl)-4,5-dihydrooxazole, (4S,5S)-4-(2-(dicyclohexyl-phosphinooxy)-1,3-diphenylpropan-2-yl)-5-methyl-2-phenyl-4,5-dihydrooxazole, (R,R)-P,N-ferrocene oxazoline, (R,R)-P,N-ferrocene imidazoline and benzoyl-(R,R)—P,N-ferrocene imidazoline.

6. The process according to claim 1, wherein at least one transition metal of the catalyst is selected from the group consisting of Cu, Co, Ni, Rh, Ru, Pd and Ir.

7. The process according to claim 1, wherein the catalyst is selected from the group consisting of (1,5-cyclooctadiene)(pyridine)(tricyclohexyl-phosphine) iridium(1) hexafluorophosphate; (1,5-cyclooctadiene)iridium(1)tetrakis[3,5-bis(trifluoromethyl)phenyl]borate (S)-2-(1-(bis(2,6-dimethylphenyl)phosphino)-2-methylpropan-2-yl)-4-tert-butyl-4,5-dihydrooxazole; (1,5-cyclooctadiene)iridium(I)tetrakis[3,5-bis(trifluoromethyl)phenyl]borate (S)-4-tert-butyl-2-(2-(diphenylphosphino)phenyl)-4,5-dihydro-oxazole; (1,5-cyclooctadiene)iridium(I)tetrakis[3,5-bis(trifluoromethyl)phenyl]borate (4S,5S)-4-(2-(dicyclohexylphosphinooxy)-1,3-diphenylpropan-2-yl)-5-methyl-2-phenyl-4,5-dihydrooxazole; (1,5-cyclooctadiene)iridium(1)tetrakis[3,5-bis(trifluoromethyl)phenyl]borate (R,R)-P,N-ferrocene oxazoline; (1,5-cyclooctadiene)iridium(I)tetrakis[3,5-bis(trifluoromethyl)phenyl]borate (R,R)-P,N-ferrocene imidazoline, (1,5-cyclooctadiene)iridium(I)tetrakis[3,5-bis-(trifluoromethyl)phenyl]borate benzoyl-(R,R)—P,N-ferrocene imidazoline, bis(1,5-cyclooctadiene)diiridium(I)dichloride (R)-(+)-2,2',6,6'-tetramethoxy-4,4'-bis(diphenylphosphino)-3,3'-bipyridine, bis(1,5-cyclooctadiene)diiridium(1)dichloride (S)-2,2',6,6'-tetramethoxy-bis[di(3,5-dimethylphenyl) phosphino]-3,3'-bipyridine; bis(1,5-cyclooctadiene) dirhodium (I)dichloride (S)-2,2',6,6'-tetramethoxy-bis[di(3,5-dimethylphenyl) phosphino]-3,3'-bipyridine; bis (cycloocta-1,5-diene)rhodium(I)tetrafluoroborate (R)-4,12-bis(diphenylphosphino)-[2.2]-paracyclophane; and benzeneruthenium(II)dichloride dimer 1-(S)—N-methyl-N-(diphenylphosphino)-1-[(R)-(diphenylphosphino)-ferrocenyl]ethylamine and bis(2-methylallyl)(1,5-cyclooctadien)ruthenium (II) (S)-(+)-4,12-bis[di(3,5-dimethylphenyl)phosphino]-[2.2]paracyclophane.

8. The process according to claim 1, wherein hydrogenation is carried out at a temperature from about 10° C. to 80° C., and/or
   wherein hydrogenation is carried out at a pressure of hydrogen of about 5 to 20 bar; and/or
   wherein the reaction time is about 1 to 20 days; and/or
   wherein a solvent for the halogenation reaction is selected from the group consisting of THF, $CH_2Cl_2$, 1,2-dichloroethane and toluene.

9. The process according to claim 1, wherein the dehalogenation occurs in less than 5 molar %, relative to the molar amount of the compound of formula VI.

10. The process according to claim 1 further comprising formulating the compound of formula VI with pharmaceutically acceptable excipients into a pharmaceutically active compound.

11. The process according to claim 6, wherein at least one transition metal of the catalyst is selected from the group consisting of Rh, Ru, Pd and Ir.

12. The process according to claim 11, wherein at least one transition metal of the catalyst is selected from the group consisting of Ru and Ir.

13. The process of claim 12, wherein said metal of the catalyst is Ir.

14. The process according to claim 8, wherein hydrogenation is carried out at a temperature from about 45° C. to 55° C., wherein the reaction time is about 10 days.

15. The process of claim 14, wherein hydrogenation is carried out at a temperature of about 50° C.

16. The process according to claim 9, wherein the dehalogenation occurs in less than 3 molar % relative to the molar amount of the compound of formula VI.

17. The process according to claim 16, wherein the dehalogenation occurs in less than 1 molar % relative to the molar amount of the compound of formula VI.

* * * * *

UNITED STATES PATENT AND TRADEMARK OFFICE
CERTIFICATE OF CORRECTION

| | | Page 1 of 1 |
|---|---|---|
| PATENT NO. | : 8,785,674 B2 | |
| APPLICATION NO. | : 13/379171 | |
| DATED | : July 22, 2014 | |
| INVENTOR(S) | : Ivana Gazic Smilovic | |

It is certified that error appears in the above-identified patent and that said Letters Patent is hereby corrected as shown below:

On the Title Page, Item (73), Assignee should read as

Lek Pharmaceuticals D.D., Ljubljana (SI)

Signed and Sealed this

Thirteenth Day of January, 2015

Michelle K. Lee
*Deputy Director of the United States Patent and Trademark Office*